US00RE49529E

(19) United States
(12) Reissued Patent
Quinn et al.

(10) Patent Number: US RE49,529 E
(45) Date of Reissued Patent: May 16, 2023

(54) METHODS OF TREATING TISSUE CALCIFICATION

(71) Applicant: Inozyme Pharma, Inc., Boston, MA (US)

(72) Inventors: Anthony Quinn, Chestnut Hill, MA (US); Nelson Hsia, Cambridge, MA (US); Tayeba Khan, Lexington, MA (US); Kim Lynette Askew, Lincoln, MA (US); Gregory Grabowski, Lexington, MA (US); Zhiliang Cheng, New Haven, CT (US); W. Charles O'Neill, Decatur, GA (US)

(73) Assignee: Inozyme Pharma, Inc., Boston, MA (US)

(21) Appl. No.: 17/111,156

(22) Filed: Dec. 3, 2020

Related U.S. Patent Documents

Reissue of:
(64) Patent No.: 10,493,135
Issued: Dec. 3, 2019
Appl. No.: 15/536,880
PCT Filed: Dec. 18, 2015
PCT No.: PCT/US2015/066646
§ 371 (c)(1),
(2) Date: Jun. 16, 2017
PCT Pub. No.: WO2016/100803
PCT Pub. Date: Jun. 23, 2016

U.S. Applications:
(60) Provisional application No. 62/249,781, filed on Nov. 2, 2015, provisional application No. 62/094,943, filed on Dec. 19, 2014.

(51) Int. Cl.

| | |
|---|---|
| ***C12N 9/16*** | (2006.01) |
| ***A61K 38/46*** | (2006.01) |
| ***C12N 9/14*** | (2006.01) |
| ***A61P 3/00*** | (2006.01) |
| ***A61P 9/00*** | (2006.01) |
| ***A61P 13/12*** | (2006.01) |

(52) U.S. Cl.
CPC ..... *A61K 38/46* (2013.01); *A61P 3/00* (2018.01); *A61P 9/00* (2018.01); *A61P 13/12* (2018.01); *C12N 9/16* (2013.01); *C12Y 301/04001* (2013.01); *C12Y 306/01009* (2013.01); *C07K 2319/30* (2013.01)

(58) Field of Classification Search
CPC ..... A61K 38/46; C12N 9/16
See application file for complete search history.

(56) References Cited

U.S. PATENT DOCUMENTS

| | | | | |
|---|---|---|---|---|
| 8,846,603 | B2 | 9/2014 | Quinn et al. | |
| 9,540,621 | B2 | 1/2017 | Quinn et al. | |
| 9,744,219 | B2 * | 8/2017 | Braddock | A61K 38/46 |
| 10,493,135 | B2 | 12/2019 | Quinn et al. | |
| 2004/0166521 | A1 | 8/2004 | Boyd et al. | |
| 2017/0145393 | A1 | 5/2017 | Quinn et al. | |
| 2018/0318400 | A1 | 11/2018 | Quinn et al. | |

FOREIGN PATENT DOCUMENTS

| | | | |
|---|---|---|---|
| JP | 2014-509851 | A | 4/2014 |
| WO | 2006039480 | A2 | 4/2006 |
| WO | 2011/113027 | A2 | 9/2011 |
| WO | 2012125182 | A1 | 9/2012 |
| WO | 2014126965 | A2 | 8/2014 |
| WO | 2016187408 | A1 | 11/2016 |
| WO | 2017087936 | A1 | 5/2017 |

OTHER PUBLICATIONS

Belli, S., et al., "Identification and characterization of a soluble form of the plasma cell membrane glycoprotein PC-1 (5'-nucleotide phosphodiesterase)," The FEBS Journal, vol. 217, 1993, pp. 421-428.

Dabisch-Ruthe, M., et al., "Variants in genes encoding pyrophosphate metabolizing enzymes are associated with Pseudoxanthoma eslasticum," Clinical Biochemsitry, 2014, vol. 47, No. 15, pp. 60-67.

Eller, P., et al., "Impact of ENPP1 genotype on arterial calcification in patients with end-stage renal failure," Nephrology, Dialysis, Transplantation, 2008, vol. 23, No. 1, pp. 321-327.

Guanabens, N., et al., "Calcific Periarthritis as the Only Clinical Manifestation of Hypophosphatasia in Middle-Aged Sisters," Journal of Bone ande Mineral Research, 2014, vol. 29, No. 4, pp. 929-934.

International Search Report and Written Opinion of the International Searching Authority from PCT/US2015/066646, Jun. 10, 2016.

Japanese Office Action for Application No. 2017-531728, issued Aug. 4, 2020, 15 pages.

Jansen, S., et al., "Structure of NPP1, an Ectonucleotide Pyrophosphatase/Phosphodiesterase Involved in Tissue Calcification", Structure, vol. 20, No. 11, Nov. 2012 , pp. 1948-1959.

Johnson, K, et al., "Linked Deficiencies in Extracellular PPi and Osteopontin Mediate Pathologic Calcification Associated With Defective PC-1 and ANK Expression", Journal of Bone and Mineral Research, vol. 18, No. 6, 2003, pp. 994-1004.

Otero, J., et al., "Severe Skeletal Toxicity From Protracted Etidronate Therapy for Generalized Arterial Calcification of Infancy," Journal of Bone and Mineral Research, 2013, vol. 28, No. 2, pp. 419-430.

(Continued)

*Primary Examiner* — Bruce R Campell
(74) *Attorney, Agent, or Firm* — Nutter McClennen & Fish LLP

(57) ABSTRACT

The present invention provides a method of treating NPP1 deficiency or NPP1-associated disease such as idiopathic infantile arterial calcification (IIAC), pseudoxanthoma elasticum, vascular calcification in chronic kidney disease (VCCKD), insulin resistance, hypophosphatemic rickets, myocardial ischemia, joint calcification, angioid streaks, and ossification of the posterior longitudinal ligament of the spine. The present invention provides a method for treating tissue calcification by administering soluble NPP1 to produce a transient increase in serum pyrophosphate levels.

21 Claims, 21 Drawing Sheets

Specification includes a Sequence Listing.

(56) References Cited

OTHER PUBLICATIONS

Russian Office Action for Application No. 2017119466, dated Jul. 14, 2021, 10 pages.
Singer, M., et al., Genes and Genomes, "Mir", Moscow, 1998, vol. 1, pp. 1-369, in Russian. English translation of relevant parts.
Stefan, C., et al., "NPP-type ectophosphodiesterases: unity in diversity", Trends in Biochemical Sciences, Elsevier, Amsterdam, NL, vol. 30, No. 10, Oct. 1, 2005, pp. 542-550.
Mexican Office Action for Mexican Patent Application No. MX/a/2017/007946, dated Sep. 14, 2021, 9 pages.
Jansen, R., et al., "ABCC6 prevents ectopic mineralization seen in pseudoxanthoma elasticum by inducing cellular nucleotide release," Proceedings of the National Academy of Sciences Dec. 2013, 110 (50), pp. 20206-20211.
Nitschke, Y., et al., "Generalized arterial calcification of infancy and pseudoxanthoma elasticum: two sides of the same coin," Frontiers in Genetics 2012, vol. 3 302, 3 pages.
Apschner, A., et al., "Pathological mineralization in a zebrafish enpp1 mutant exhibits features of Generalized Arterial Calcification of Infancy (GACI) and Pseudoxanthoma Elasticum (PXE)", Disease Models & Mechanisms, Jul. 1, 2014, 21 pages.
Dabisch-Ruthe, M., et al., "Pyrophosphates as a major inhibitor of matrix calcification in Pseudoxanthoma elasticum," Journal of Dermatological Science, Elsevier, Amsterdam, NL, vol. 75, No. 2, May 17, 2014, pp. 109-120.
Extended European Search Report for Application No. 21192925.2, issued Feb. 10, 2022 (14 pages).
Albright, R., et al., "ENPP1-Fc prevents mortality and vascular calcifications in rodent model of generalized arterial calcification of infancy", Nature Communications, vol. 6, No. 1, Dec. 1, 2015 (Dec. 1, 2015), pp. 1-11.
Goding, J W., et al., "Physiological and pathophysiological functions of the ecto-nucleotide pyrophosphatase/phosphodiesterase family", Biochimica Et Biophysica Acta. Molecular Basis of Dise, Amsterdam, NL, vol. 1638, No. 1, May 20, 2003 (May 20, 2003), pp. 1-19.
Terkeltaub, R., "Physiologic and pathologic functions of the NPP nucleotide pyrophosphatase/phosphodiesterase family focusing on NPP1 in calcification", Purinergic Signalling, Kluwer Academic Publishers, DO, vol. 2, No. 2, Jun. 1, 2012 (Jun. 1, 2012), pp. 371-377.
Jansen, S., et al., "Structure of NPP1, an Ectonucleotide Pyrophosphatase/Phosphodiesterase Involved in Tissue Calcification", Structure, vol. 20, No. 11, Nov. 1, 2012 (Nov. 1, 2012), pp. 1948-1959.
Johnson, K, et al., "Linked Deficiencies in Extracellular PPi and Osteopontin Mediate Pathologic Calcification Associated With Defective PC-1 and ANK Expression", Journal of Bone and Mineral Research, Jun. 1, 2003 (Jun. 1, 2003), pp. 994-1004.
Rezg, R., et al., "Inhibitors of Vascular Calcification as Potential Therapeutic Targets", J. Nephrol, Jul.-Aug. 2011, vol. 24, No. 4: pp. 416-427.

* cited by examiner

NPP1 (wild-type full length)

MERDGCAGGGSRGGEGGRAPREGPAGNGRDRGRSHAAEAPGDPQAAASLLAPMDVGEEPLEKAARA
RTAKDPNTYKVLSLVLSVCVLTTILGCIFGLKPSCAKEVKSCKGRCFERTFGNCRCDAACVELGNCCLDYQET
CIEPEHIWTCNKFRCGEKRLTRSLCACSDDCKDKGDCCINYSSVCQGEKSWVEEPCESINEPQCPAGFETP
PTLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV
LQWLQLPKDERPHFYTLYLEEPDSSGHSYGPVSSEVIKALQRVDGMVGMLMDGLKELNLHRCLNLILISD
HGMEQGSCKKYIYLNKYLGDVKNIKVIYGPAARLRPSDVPDKYYSFNYEGIARNLSCREPNQHFKPYLKHF
LPKRLHFAKSDRIEPLTFYLDPQWQLALNPSERKYCGSGFHGSDNVFSNMQALFVGYGPGFKHGIEADTF
ENIEVYNLMCDLLNLTPAPNNGTHGSLNHLLKNPVYTPKHPKEVHPLVQCPFTRNPRDNLGCSCNPSILPI
EDFQTQFNLTVAEEKIIKHETLPYGRPRVLQKENTICLLSQHQFMSGYSQDILMPLWTSYTVDRNDSFSTE
DFSNCLYQDFRIPLSPVHKCSFYKNNTKVSYGFLSPPQLNKNSSGIYSEALLTTNIVPMYQSFQVIWRYFHD
TLLRKYAEERNGVNVVSGPVFDFDYDGRCDSLENLRQKRRVIRNQEILIPTHFFIVLTSCKDTSQTPLHCENL
DTLAFILPHRTDNSESCVHGKHDSSWVEELLMLHRARITDVEHITGLSFYQQRKEPVSDILKLKTHLPTFSQ
ED (SEQ ID NO:1)

Fig. 1 sNPP1

PSCAKEVKSCKGRCFERTFGNCRCDAACVELGNCCLDYQETCIEPEHIWTCNKFRCGEKRLTRSLCACSD
DCKDKGDCCINYSSVCQGEKSWVEEPCESINEPQCPAGFETPPTLLFSLDGFRAEYLHTWGGLLPVISKLK
KCGTYTKNMRPVYPTKTFPNHYSIVTGLYPESHGIIDNKMYDPKMNASFSLKSKEKFNPEWYKGEPIWVT
AKYQGLKSGTFFWPGSDVEINGIFPDIYKMYNGSVPFEERILAVLQWLQLPKDERPHFYTLYLEEPDSSGH
SYGPVSSEVIKALQRVDGMVGMLMDGLKELNLHRCLNLILISDHGMEQGSCKKYIYLNKYLGDVKNIKVI
YGPAARLRPSDVPDKYYSFNYEGIARNLSCREPNQHFKPYLKHFLPKRLHFAKSDRIEPLTFYLDPQWQLA
LNPSERKYCGSGFHGSDNVFSNMQALFVGYGPGFKHGIEADTFENIEVYNLMCDLLNLTPAPNNGTHGS
LNHLLKNPVYTPKHPKEVHPLVQCPFTRNPRDNLGCSCNPSILPIEDFQTQFNLTVAEEKIIKHETLPYGRP
RVLQKENTICLLSQHQFMSGYSQDILMPLWTSYTVDRNDSFSTEDFSNCLYQDFRIPLSPVHKCSFYKNN
TKVSYGFLSPPQLNKNSSGIYSEALLTTNIVPMYQSFQVIWRYFHDTLLRKYAEERNGVNVVSGPVFDFDY
DGRCDSLENLRQKRRVIRNQEILIPTHFFIVLTSCKDTSQTPLHCENLDTLAFILPHRTDNSESCVHGKHDSS
WVEELLMLHRARITDVEHITGLSFYQQRKEPVSDILKLKTHLPTFSQED (SEQ ID NO:2)

Fig. 2

NPP1-Fc

PSCAKEVKSCKGRCFERTFGNCRCDAACVELGNCCLDYQETCIEPEHIWTCNKFRCGEKRLTRSLCACSD
DCKDKGDCCINYSSVCQGEKSWVEEPCESINEPQCPAGFETPPTLLFSLDGFRAEYLHTWGGLLPVISKLK
KCGTYTKNMRPVYPTKTFPNHYSIVTGLYPESHGIIDNKMYDPKMNASFSLKSKEKFNPEWYKGEPIWVT
AKYQGLKSGTFFWPGSDVEINGIFPDIYKMYNGSVPFEERILAVLQWLQLPKDERPHFYTLYLEEPDSSGH
SYGPVSSEVIKALQRVDGMVGMLMDGLKELNLHRCLNLILISDHGMEQGSCKKYIYLNKYLGDVKNIKVI
YGPAARLRPSDVPDKYYSFNYEGIARNLSCREPNQHFKPYLKHFLPKRLHFAKSDRIEPLTFYLDPQWQLA
LNPSERKYCGSGFHGSDNVFSNMQALFVGYGPGFKHGIEADTFENIEVYNLMCDLLNLTPAPNNGTHGS
LNHLLKNPVYTPKHPKEVHPLVQCPFTRNPRDNLGCSCNPSILPIEDFQTQFNLTVAEEKIIKHETLPYGRP
RVLQKENTICLLSQHQFMSGYSQDILMPLWTSYTVDRNDSFSTEDFSNCLYQDFRIPLSPVHKCSFYKNN
TKVSYGFLSPPQLNKNSSGIYSEALLTTNIVPMYQSFQVIWRYFHDTLLRKYAEERNGVNVVSGPVFDFDY
DGRCDSLENLRQKRRVIRNQEILIPTHFFIVLTSCKDTSQTPLHCENLDTLAFILPHRTDNSESCVHGKHDSS
WVEELLMLHRARITDVEHITGLSFYQQRKEPVSDILKLKTHLPTFSQEDPKSCDKTHTCPPCPAPEAAGAP
SVFLFPPKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAV
EWESNGQPENNYKTTPPVLDSDGSFFLYS KLTVDKSRWQQGNVFSCSVMHEALHNHYTQKSLSLSPGK (SEQ ID NO:3)

Fig. 3

NPP1-Fc-D10

PSCAKEVKSCKGRCFERTFGNCRCDAACVELGNCCLDYQETCIEPEHIWTCNKFRCGEKRLTRSLCACSD
DCKDKGDCCINYSSVCQGEKSWVEEPCESINEPQCPAGFETPPTLLFSLDGFRAEYLHTWGGLLPVISKLK
KCGTYTKNMRPVYPTKTFPNHYSIVTGLYPESHGIIDNKMYDPKMNASFSLKSKEKFNPEWYKGEPIWVT
AKYQGLKSGTFFWPGSDVEINGIFPDIYKMYNGSVPFEERILAVLQWLQLPKDERPHFYTLYLEEPDSSGH
SYGPVSSEVIKALQRVDGMVGMLMDGLKELNLHRCLNLILISDHGMEQGSCKKYIYLNKYLGDVKNIKVI
YGPAARLRPSDVPDKYYSFNYEGIARNLSCREPNQHFKPYLKHFLPKRLHFAKSDRIEPLTFYLDPQWQLA
LNPSERKYCGSGFHGSDNVFSNMQALFVGYGPGFKHGIEADTFENIEVYNLMCDLLNLTPAPNNGTHGS
LNHLLKNPVYTPKHPKEVHPLVQCPFTRNPRDNLGCSCNPSILPIEDFQTQFNLTVAEEKIIKHETLPYGRP
RVLQKENTICLLSQHQFMSGYSQDILMPLWTSYTVDRNDSFSTEDFSNCLYQDFRIPLSPVHKCSFYKNN
TKVSYGFLSPPQLNKNSSGIYSEALLTTNIVPMYQSFQVIWRYFHDTLLRKYAEERNGVNVVSGPVFDFDY
DGRCDSLENLRQKRRVIRNQEILIPTHFFIVLTSCKDTSQTPLHCENLDTLAFILPHRTDNSESCVHGKHDSS
WVEELLMLHRARITDVEHITGLSFYQQRKEPVSDILKLKTHLPTFSQEDPKSCDKTHTCPPCPAPEAAGAP
SVFLFPPKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALHNHYTQKSLSLSPGK
DDDDDDDDDD

(SEQ ID NO:4)

Fig. 4

SCKGRCFERTFGNCRCDAACVELGNCCLDYQETCIEPEHIWTCNKFRCGEKRLTRSLCACSDDCKDKGDCC
INYSSVCQGEKSWVEEPCESINEPQCPAGFETPPTLLFSLDGFRAEYLHTWGGLLPVISKLKKCGTYTKNM
RPVYPTKTFPNHYSIVTGLYPESHGIIDNKMYDPKMNASFSLKSKEKFNPEWYKGEPIWVTAKYQGLKSGT
FFWPGSDVEINGIFPDIYKMYNGSVPFEERILAVLQWLQLPKDERPHFYTLYLEEPDSSGHSYGPVSSEVIK
ALQRVDGMVGMLMDGLKELNLHRCLNLILISDHGMEQGSCKKYIYLNKYLGDVKNIKVIYGPAARLRPSD
VPDKYYSFNYEGIARNLSCREPNQHFKPYLKHFLPKRLHFAKSDRIEPLTFYLDPQWQLALNPSERKYCGSG
FHGSDNVFSNMQALFVGYGPGFKHGIEADTFENIEVYNLMCDLLNLTPAPNNGTHGSLNHLLKNPVYTP
KHPKEVHPLVQCPFTRNPRDNLGCSCNPSILPIEDFQTQFNLTVAEEKIIKHETLPYGRPRVLQKENTICLLS
QHQFMSGYSQDILMPLWTSYTVDRNDSFSTEDFSNCLYQDFRIPLSPVHKCSFYKNNTKVSYGFLSPPQL
NKNSSGIYSEALLTTNIVPMYQSFQVIWRYFHDTLLRKYAEERNGVNVVSGPVFDFDYDGRCDSLENLRQ
KRRVIRNQEILIPTHFFIVLTSCKDTSQTPLHCENLDTLAFILPHRTDNSESCVHGKHDSSWVEELLMLHRA
RITDVEHITGLSFYQQRKEPVSDILKLKTHLPTFSQED (SEQ ID NO:5)

Fig. 12A

EKSWVEEPCESINEPQCPAGFETPPTLLFSLDGFRAEYLHTWGGLLPVISKLKKCGTYTKNMRPVYPTKTF
PNHYSIVTGLYPESHGIIDNKMYDPKMNASFSLKSKEKFNPEWYKGEPIWVTAKYQGLKSGTFFWPGSD
VEINGIFPDIYKMYNGSVPFEERILAVLQWLQLPKDERPHFYTLYLEEPDSSGHSYGPVSSEVIKALQRVDG
MVGMLMDGLKELNLHRCLNLILISDHGMEQGSCKKYIYLNKYLGDVKNIKVIYGPAARLRPSDVPDKYYS
FNYEGIARNLSCREPNQHFKPYLKHFLPKRLHFAKSDRIEPLTFYLDPQWQLALNPSERKYCGSGFHGSDN
VFSNMQALFVGYGPGFKHGIEADTFENIEVYNLMCDLLNLTPAPNNGTHGSLNHLLKNPVYTPKHPKEV
HPLVQCPFTRNPRDNLGCSCNPSILPIEDFQTQFNLTVAEEKIIKHETLPYGRPRVLQKENTICLLSQHQFM
SGYSQDILMPLWTSYTVDRNDSFSTEDFSNCLYQDFRIPLSPVHKCSFYKNNTKVSYGFLSPPQLNKNSSG
IYSEALLTTNIVPMYQSFQVIWRYFHDTLLRKYAEERNGVNVVSGPVFDFDYDGRCDSLENLRQKRRVIR
NQEILIPTHFFIVLTSCKDTSQTPLHCENLDTLAFILPHRTDNSESCVHGKHDSSWVEELLMLHRARITDVE
HITGLSFYQQRKEPVSDILKLKTHLPTFSQED (SEQ ID NO:6)

Fig. 12B

Fc (including hinge region)

EPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSRWQQGNVFSC
SVMHEALHNHYTQKSLSLSPGK (SEQ ID NO:7)

Fig. 12C

Fc (partial hinge Fc)

DKTHTCPPCPAPELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQGNVFSCSVM
HEALHNHYTQKSLSLSPGK (SEQ ID NO:8)

Fig. 12D

(107-925)-Fc

SCKGRCFERTFGNCRCDAACVELGNCCLDYQETCIEPEHIWTCNKFRCGEKRLTRSLCACSDDCKDKGDCC
INYSSVCQGEKSWVEEPCESINEPQCPAGFETPPTLLFSLDGFRAEYLHTWGGLLPVISKLKKCGTYTKNM
RPVYPTKTFPNHYSIVTGLYPESHGIIDNKMYDPKMNASFSLKSKEKFNPEWYKGEPIWVTAKYQGLKSGT
FFWPGSDVEINGIFPDIYKMYNGSVPFEERILAVLQWLQLPKDERPHFYTLYLEEPDSSGHSYGPVSSEVIK
ALQRVDGMVGMLMDGLKELNLHRCLNLILISDHGMEQGSCKKYIYLNKYLGDVKNIKVIYGPAARLRPSD
VPDKYYSFNYEGIARNLSCREPNQHFKPYLKHFLPKRLHFAKSDRIEPLTFYLDPQWQLALNPSERKYCGSG
FHGSDNVFSNMQALFVGYGPGFKHGIEADTFENIEVYNLMCDLLNLTPAPNNGTHGSLNHLLKNPVYTP
KHPKEVHPLVQCPFTRNPRDNLGCSCNPSILPIEDFQTQFNLTVAEEKIIKHETLPYGRPRVLQKENTICLLS
QHQFMSGYSQDILMPLWTSYTVDRNDSFSTEDFSNCLYQDFRIPLSPVHKCSFYKNNTKVSYGFLSPPQL
NKNSSGIYSEALLTTNIVPMYQSFQVIWRYFHDTLLRKYAEERNGVNVVSGPVFDFDYDGRCDSLENLRQ
KRRVIRNQEILIPTHFFIVLTSCKDTSQTPLHCENLDTLAFILPHRTDNSESCVHGKHDSSWVEELLMLHRA
RITDVEHITGLSFYQQRKEPVSDILKLKTHLPTFSQEDEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK (SEQ ID NO:9)

Fig. 12E

(107-925)-partial hinge Fc

SCKGRCFERTFGNCRCDAACVELGNCCLDYQETCIEPEHIWTCNKFRCGEKRLTRSLCACSDDCKDKGDCC
INYSSVCQGEKSWVEEPCESINEPQCPAGFETPPTLLFSLDGFRAEYLHTWGGLLPVISKLKKCGTYTKNM
RPVYPTKTFPNHYSIVTGLYPESHGIIDNKMYDPKMNASFSLKSKEKFNPEWYKGEPIWVTAKYQGLKSGT
FFWPGSDVEINGIFPDIYKMYNGSVPFEERILAVLQWLQLPKDERPHFYTLYLEEPDSSGHSYGPVSSEVIK
ALQRVDGMVGMLMDGLKELNLHRCLNLILISDHGMEQGSCKKYIYLNKYLGDVKNIKVIYGPAARLRPSD
VPDKYYSFNYEGIARNLSCREPNQHFKPYLKHFLPKRLHFAKSDRIEPLTFYLDPQWQLALNPSERKYCGSG
FHGSDNVFSNMQALFVGYGPGFKHGIEADTFENIEVYNLMCDLLNLTPAPNNGTHGSLNHLLKNPVYTP
KHPKEVHPLVQCPFTRNPRDNLGCSCNPSILPIEDFQTQFNLTVAEEKIIKHETLPYGRPRVLQKENTICLLS
QHQFMSGYSQDILMPLWTSYTVDRNDSFSTEDFSNCLYQDFRIPLSPVHKCSFYKNNTKVSYGFLSPPQL
NKNSSGIYSEALLTTNIVPMYQSFQVIWRYFHDTLLRKYAEERNGVNVVSGPVFDFDYDGRCDSLENLRQ
KRRVIRNQEILIPTHFFIVLTSCKDTSQTPLHCENLDTLAFILPHRTDNSESCVHGKHDSSWVEELLMLHRA
RITDVEHITGLSFYQQRKEPVSDILKLKTHLPTFSQEDDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO:10)

Fig. 12F

(187-925)-Fc

EKSWVEEPCESINEPQCPAGFETPPTLLFSLDGFRAEYLHTWGGLLPVISKLKKCGTYTKNMRPVYPTKTF
PNHYSIVTGLYPESHGIIDNKMYDPKMNASFSLKSKEKFNPEWYKGEPIWVTAKYQGLKSGTFFWPGSD
VEINGIFPDIYKMYNGSVPFEERILAVLQWLQLPKDERPHFYTLYLEEPDSSGHSYGPVSSEVIKALQRVDG
MVGMLMDGLKELNLHRCLNLILISDHGMEQGSCKKYIYLNKYLGDVKNIKVIYGPAARLRPSDVPDKYYS
FNYEGIARNLSCREPNQHFKPYLKHFLPKRLHFAKSDRIEPLTFYLDPQWQLALNPSERKYCGSGFHGSDN
VFSNMQALFVGYGPGFKHGIEADTFENIEVYNLMCDLLNLTPAPNNGTHGSLNHLLKNPVYTPKHPKEV
HPLVQCPFTRNPRDNLGCSCNPSILPIEDFQTQFNLTVAEEKIIKHETLPYGRPRVLQKENTICLLSQHQFM
SGYSQDILMPLWTSYTVDRNDSFSTEDFSNCLYQDFRIPLSPVHKCSFYKNNTKVSYGFLSPPQLNKNSSG
IYSEALLTTNIVPMYQSFQVIWRYFHDTLLRKYAEERNGVNVVSGPVFDFDYDGRCDSLENLRQKRRVIR
NQEILIPTHFFIVLTSCKDTSQTPLHCENLDTLAFILPHRTDNSESCVHGKHDSSWVEELLMLHRARITDVE
HITGLSFYQQRKEPVSDILKLKTHLPTFSQEDEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO:11)

Fig. 12G

(187-925)-partial hinge Fc

EKSWVEEPCESINEPQCPAGFETPPTLLFSLDGFRAEYLHTWGGLLPVISKLKKCGTYTKNMRPVYPTKTF
PNHYSIVTGLYPESHGIIDNKMYDPKMNASFSLKSKEKFNPEWYKGEPIWVTAKYQGLKSGTFFWPGSD
VEINGIFPDIYKMYNGSVPFEERILAVLQWLQLPKDERPHFYTLYLEEPDSSGHSYGPVSSEVIKALQRVDG
MVGMLMDGLKELNLHRCLNLILISDHGMEQGSCKKYIYLNKYLGDVKNIKVIYGPAARLRPSDVPDKYYS
FNYEGIARNLSCREPNQHFKPYLKHFLPKRLHFAKSDRIEPLTFYLDPQWQLALNPSERKYCGSGFHGSDN
VFSNMQALFVGYGPGFKHGIEADTFENIEVYNLMCDLLNLTPAPNNGTHGSLNHLLKNPVYTPKHPKEV
HPLVQCPFTRNPRDNLGCSCNPSILPIEDFQTQFNLTVAEEKIIKHETLPYGRPRVLQKENTICLLSQHQFM
SGYSQDILMPLWTSYTVDRNDSFSTEDFSNCLYQDFRIPLSPVHKCSFYKNNTKVSYGFLSPPQLNKNSSG
IYSEALLTTNIVPMYQSFQVIWRYFHDTLLRKYAEERNGVNVVSGPVFDFDYDGRCDSLENLRQKRRVIR
NQEILIPTHFFIVLTSCKDTSQTPLHCENLDTLAFILPHRTDNSESCVHGKHDSSWVEELLMLHRARITDVE
HITGLSFYQQRKEPVSDILKLKTHLPTFSQEDDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO:12)

Fig. 12H

METHODS OF TREATING TISSUE CALCIFICATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

[This application is a United States National Phase under 35 U.S.C. § 371 of International Application No. PCT/US2015/066646, filed on Dec. 18, 2015, which claims the benefit of U.S. Provisional Application 62/094,943, filed on Dec. 19, 2014 and U.S. Provisional Application No. 62/249,781, filed on Nov. 2, 2015. The entire teachings of the above applications are incorporated herein by reference.] *This application is a reissue of U.S. Pat. No. 10,493,135, issued Dec. 3, 2019, which issued from U.S. patent application Ser. No. 15/536,880, filed Mar. 16, 2017, which is a United States National Phase under 35 U.S.C. § 371 of International Application No. PCT/US2015/066646, filed on Dec. 18, 2015, which claims the benefit of U.S. Provisional Application No. 62/094,943, filed on Dec. 19, 2014 and U.S. Provisional Application No. 62/249,781, filed on Nov. 2, 2015. The entire teachings of the above applications are incorporated herein by reference.*

REFERENCE TO SEQUENCE LISTING SUBMITTED ELECTRONICALLY

The content of the electronically submitted sequence listing in ASCII text file (Name: 081245-0208_ascii.txt; Size: 88,556 bytes; and Date of Creation: Dec. 15, 2015) filed with the application is incorporated herein by reference in its entirety.

BACKGROUND OF THE INVENTION

Vascular calcification can be characterized by formation of very small, dispersed crystals of hydroxyapatite (HA) and as large calcified deposits in vascular tissue, such as arteries. (Amann, K. Clin J Am Soc Nephrol 2008, 3, 1599-605). Extracellular pyrophosphate (PPi) is a key endogenous inhibitor of vascular calcification by inhibiting HA formation. (Lomashvili, K. A. et al., J Am Soc Nephrol 2004, 15, 1392-1401; Fleisch, H. et al., Nature 1966, 212, 901-903).

Ectonucleotide pyrophosphatase pyrophosphorylase (NPP1) is an ectoenzyme that cleaves ATP to produce extracellular pyrophosphate (PPi). Pyrophosphate is a potent inhibitor of hydroxyapatite formation and, under normal conditions, functions to inhibit vascular calcification.

Deficiency of NPP1 in humans results in reduced circulating PPi levels and has been implicated in conditions such as arterial calcification and generalized arterial calcification of infancy (GACI). (Rutsch, F. et al., Am J Pathol 2001, 158, 543-554). When fed a high-phosphate diet, mice lacking NPP1 (Enpp1$^{-/-}$) also have reduced PPi levels and exhibit a similar phenotype as NPP1 deficient humans. (Harmey, D. et al., Am J Pathol 2004, 164, 1199-1209). Vascular calcification is also a well-recognized and common complication in chronic kidney disease (CKD) and end-stage renal disease (ESRD) subjects, and is associated with increased morbidity and mortality. (Giachelli, C. J Am Soc Nephrol 2004, 15, 2959-64; Raggi, P. et al., J Am Coll Cardiol 2002, 39, 695-701).

Ectonucleotide pyrophosphatase/phosphodiesterase 1 (NPP1/ENPP1/PC-1) deficiency is a rare disease caused by mutations in NPP1, a type II transmembrane glycoprotein. NPP1 cleaves a variety of substrates, including phosphodiester bonds of nucleotides and nucleotide sugars and pyrophosphate bonds of nucleotides and nucleotide sugars. NPP1 deficiency has been associated with idiopathic infantile arterial calcification (IIAC), insulin resistance, hypophosphatemic rickets, and ossification of the posterior longitudinal ligament of the spine.

IIAC, a rare autosomal recessive and nearly always fatal disorder, is characterized by calcification of the internal elastic lamina of muscular arteries and stenosis due to myointimal proliferation. There are more than 160 cases of IIAC that have been reported world-wide. The symptoms of the disease most often appear by early infancy, and the disease is lethal by 6 months of age, generally because of ischemic cardiomyopathy, and other complications of obstructive arteriopathy including renal artery stenosis.

Although defects in the NPP1 protein have been implicated in such serious disease as IIAC, currently no treatment is available for those who are affected by the disease and other calcification diseases caused by high total body burden of calcium and phosphorus due to abnormal bone metabolism; low levels of circulating and locally produced inhibitors of phosphate producers; or impaired renal excretion.

Current therapeutic options to prevent vascular calcification have limited efficacy and undesirable and/or unacceptable side effects. For example, very large quantities of exogenous PPi are needed for efficacy and other inhibitors hydroxyapatite formation inhibit calcification of bone and can lead to osteomalacia. In particular, direct administration of exogenous PPi was found to prevent calcification in uremic animal models. (O'Neil, W. C. et al., Kidney Int 2011, 79, 512-517; Riser, B. L. et al., Nephrol Dial Transp 2011, 26, 3349-3357). But, this approach required high doses of PPi, due to the short half-life of PPi, and resulted in supraphysiologic plasma levels of PPi leading to local irritation. Bisphosphonates, which are non-hydrolyzable analogs of PPi, have been used to treat vascular calcification, e.g., in animal models. (Fleisch, H. et al., Europ J Clin Invest 1970, 1, 12-18; Price, P. A. et al., Arteriosclerosis Throm and Vas Bio 2001, 21, 817-824; Price, P. A. et al., Kidney Int 2006, 70, 1577-1583; Lomashvili, K. A. et al., Kidney Int 2009, 75, 617-625). However, bisphosphonates also inhibit bone formation. Bisphosphonates can delay but not stop calcification in subjects with GACI (Rutsch, F. et al., Circ Cardiovasc Genet 2008, 1, 133-140), and, as in animals, lead to osteomalacia. (Otero, J. E., et al., J Bone Miner Res 2013, 28, 419-430).

Braddock, D. et al., (WO 2014/126965A2) discloses compositions and methods for treating pathological calcification and ossification by administering NPP1. Quinn, A. et al., (WO 2012/125182A1) discloses a NPP1 fusion protein to treat conditions including GACI, arterial calcification, insulin resistance, hypophasphatemic rickets, and ossificaiton of the posterior longitudinal ligament of the spine.

In spite of considerable research in the field, there is a continuing need for new therapies to effectively inhibit vascular calicification, preferably without causing osteomalacia. There is also a need for an effective and safe medicament for the treatment of IIAC, vascular calcification in chronic kidney disease (VCCKD), pseudoxanthoma elasticum (PXE), insulin resistance, hypophosphatemic rickets, and ossification of the posterior longitudinal ligament of the spine.

SUMMARY OF THE INVENTION

The present invention relates to uses of isolated recombinant human soluble NPP1 that lacks N-terminal cytosolic and transmembrane domains and fusion proteins thereof for the treatment of NPP1-deficiency or other progressive disorders characterized by the accumulation of deposits of calcium and other minerals.

The proteins of the invention can be surprisingly used to restore blood NPP1 activity and restore normal level of pyrophosphate in subjects having deficiencies in NPP1 activity or exhibiting accumulation of calcium deposits in the bones, joints, heart, blood vessels, eyes, and/or the skin.

More specifically, the NPP1 proteins and NPP1 fusion proteins of the invention can be used to treat subjects having NPP1-deficiency or other diseases or disorders associated with low levels of pyrophosphate, including but not limited to, idiopathic infantile arterial calcification (IIAC, also known as general arterial calcification in infants), vascular calcification in chronic kidney disease (VCCKD), pseudoxanthoma elasticum (PXE), insulin resistance, hypophosphatemic rickets, joint calcification, myocardial ischemia, and ossification of the posterior longitudinal ligament of the spine. Any progressive disorder that is characterized by the accumulation of deposits of calcium and other minerals in arterial and/or connective tissues are within the scope of the present invention.

In some aspects, the invention relates to a method of reducing tissue calcification, preferably vascular calcification in a subject in need thereof. The method comprises administering to a subject with low plasma pyrophosphate (PPi) or elevated inorganic phosphate (Pi), two or more doses of a therapeutically effective amount of a composition comprising a soluble ectonucleotide pyrophosphatase phosphodiesterase (NPP1). Each dose contains an amount of soluble NPP1 that is sufficient to achieve a transient increase in plasma PPi in the subject. The transient increase in plasma PPi characterized by a peak PPi level that is at least about 40% of the normal plasma PPi level and a return to base-line PPi level within about 48 hours after administration of the dose. The time period between doses is at least 2 days.

The transient increase in plasma PPi is maintained for at least about 4 hours, preferably, at least about 6 hours, at least about 8 hours, at least about 10 hours or at least about 12 hours.

The tissue calcification can be vascular calcification, such as venous or arterial calcification, and the calcification can be intimal or medial.

The subject in need of therapy may have NPP1 deficiency, chronic kidney disease (CKD), end-stage renal disease (ESRD), generalized arterial calcification of infancy (GACI), cardiovascular disorder, diabetes mellitus II, atherosclerosis or pseudoxanthoma elasticum (PXE). When the subject has low plasma PPi, the pretreatment levels of plasma pyrophosphate (PPi) in the subject is at least about 40% lower than that of the normal plasma PPi levels and the subject is human. When the subject has high levels of Pi, the pretreatment levels of Pi in the subject are typically at least about 110% of the normal plasma Pi levels.

The amount of sNPP1 administered in each dose can be about 1.0 mg/kg to about 5.0 mg/kg NPP1 or about 1.0 mg/kg to about 10.0 mg/kg NPP1. The time period between doses of NPP1 is at least 2 days and can be longer, for example at least 3 days, at least 1 week, 2 weeks or 1 month. The sNPP1 can be administered in any suitable way, such as intravenously, subcutaneously, or intraperitoneally.

In preferred aspects, a NPP1 fusion protein is administered. Preferred fusion proteins comprise and NPP1 component an Fc region of an immunoglobulin and optionally a targeting moiety. A preferred targeting moiety is $Asp_{10}$. Particularly preferred NPP1 fusion proteins for administration in accordance with the methods disclosed herein have the amino acid sequence of SEQ ID NO:3, SEQ ID NO:4, SEQ ID NO:9, SEQ ID NO:10, SEQ ID NO:11 or SEQ ID NO:12.

Other features and advantages of the invention will be apparent from the following detailed description and claims.

BRIEF DESCRIPTION OF THE DRAWINGS

FIG. 1 is the amino acid sequence of wild-type NPP1 protein (SEQ ID NO:1). The cytosolic and transmembrane regions are underlined. The potential N-glycosylation sites are in bold. The amino acid motif "PSCAKE" (SEQ ID NO:17) in bold is the start of a soluble NPP1 which includes the cysteine rich region.

FIG. 2 is the amino acid sequence of a sNPP1 that contains the cysteine-rich region, catalytic region and c-terminal region (SEQ ID NO:2).

FIG. 3 is the amino acid sequence of sNPP1-Fc fusion protein (SEQ ID NO:3).

FIG. 4 is the amino acid sequence of sNPP1-Fc-D10 (SEQ ID NO:4). The Fc sequence is underlined. The D10 (SEQ ID NO:18) targeting moiety is in bold.

FIGS. 12A-12H are the amino acid sequences of soluble NPP1 compounds, fusion partners and fusion proteins. FIG. 12A shows the amino acid sequences of a soluble NPP1 containing amino acids from 107 to 925 of SEQ ID NO:1 (SEQ ID NO:5). FIG. 12B shows the amino acid sequence of a soluble NPP1 containing amino acids from 187 to 925 of SEQ ID NO:1 (SEQ ID NO:6). FIG. 12C shows the amino acid sequence of the Fc region of human IgG1 including the hinge region (SEQ ID NO:7). FIG. 12D shows the amino acid sequence of the Fc of human IgG1 including a partial hinge region (SEQ ID NO:8). FIG. 12E shows the amino acid sequence of a NPP1-Fc fusion protein (SEQ ID NO:9). The NPP1 component contains SEQ ID NO:5, and the Fc sequence includes the hinge region. FIG. 12F shows the amino acid sequence of a NPP1-Fc fusion protein (SEQ ID NO:10). The soluble NPP1 contains SEQ ID NO:5, and the Fc sequence includes the partial hinge region. FIG. 12G shows the amino acid sequence of a NPP1-Fc fusion protein (SEQ ID NO:11). The soluble NPP1 contains SEQ ID NO:6, and the Fc sequence includes the hinge region. FIG. 12H shows the amino acid sequence of a NPP1-Fc fusion protein (SEQ ID NO:12). The soluble NPP1 contains SEQ ID NO:6, and the Fc sequence includes the partial hinge region.

FIG. 13A: 100 nM ATP incubated with 130 ug/ml sNPP1-Fc-D10 for one hour at 37° C. FIG. 13B: 100 nM ATP incubated with plasma from wild-type mice (WT), Enpp1$^{-/-}$ mice, and Enpp1$^{-/-}$ mice 2 hours after IV injection of recombinant NPP1 (6 mg/kg). FIG. 13C: 100 nM ATP incubated with aorta from wild-type mice (WT), Enpp1$^{-/-}$ mice, and Enpp1$^{-/-}$ mice 2 hours after IV injection of recombinant NPP1 (6 mg/kg). Pi: orthophosphate; ATP: Adenosine triphosphate; PPi: pyrophosphate.

FIG. 16A: Heparinized blood or plasma obtained from the same blood sample. FIG. 16B: Centrifuged blood cells with (all cells) or without buffy coat (erythrocytes) removed, suspended in HEPES-buffered saline. FIG. 16C: Isolated leukocytes or platelets, suspended in HEPES-buffered saline. Samples were incubated at 37° C. for 2 hours with or without recombinant NPP1 (145 ug/ml).

DETAILED DESCRIPTION OF THE INVENTION

Definitions

Figure 5:
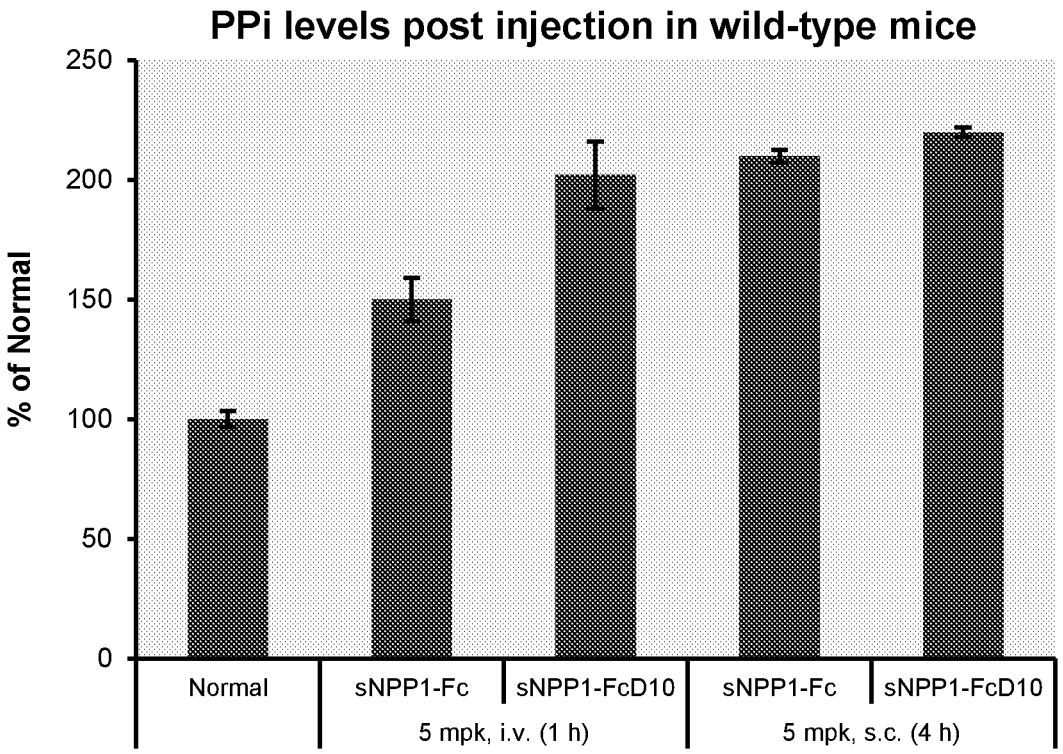
FIG. 5 illustrates pyrophosphate levels in blood in wild-type mice after administration of sNPP1-Fc or sNPP1-FcD10 intravenously (1 hour post injection) and subcutaneously (4 hour post injection).

Unless defined otherwise, all technical and scientific terms used herein have the same meaning as commonly understood by one of ordinary skill in the art to which this invention belongs. Although any methods and materials similar or equivalent to those described herein can be used in practice or testing of the present invention, the preferred methods and materials are described.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "altered PPi:Pi ratio" refers to a ratio of PPi in plasma to Pi in serum that is at least 10% or at least 20% higher or lower than a normal PPi:Pi ratio for that type of subject (e.g. a human). An altered PPi:Pi ratio can be present because of lower than normal levels of plasma PPi or higher than normal levels of serum Pi. The ratio of PPi:Pi is expressed as ([PPi]/[Pi])*1000, and the normal ratio of a human is about 1.75.

As used herein, the term "fragment", with regard to NPP1 proteins, refers to a subsequence of the full-length NPP1. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between). The fragments may range in size from four amino acid residues to the entire amino acid sequence minus one amino acid. Thus, a protein "comprising at least a portion of the amino acid sequence of SEQ ID NO: 1" encompasses the full-length NPP1 and fragments thereof.

The term "high serum Pi" as used herein refers to a level of inorganic phosphate (Pi) in the serum of a subject that is at least 110% of the normal level of Pi for that type of subject (e.g. a human). Preferably, the level of Pi in the serum of the subject at least about 120%, at least about 150%, at least about 200% or at least about 300% of the normal level of Pi for that type of subject. Normal Pi levels for a human are reported to be 1.5±0.5 millimolar (Rutsch, F. et al., Circ Cardiovasc Genet 1:133-140 (2008)).

An "isolated" or "purified" soluble NPP1 protein or biologically active fragment or fusion protein thereof is substantially free of cellular material or other contaminating proteins from the cell or tissue source from which the NPP1 protein, biologically active fragment or NPP1 fusion protein is derived, or substantially free from chemical precursors or other chemicals when chemically synthesized. The language "substantially free of cellular material" includes preparations of NPP1 protein, biologically active fragment, or NPP1 fusion protein in which the protein is separated from cellular components of the cells from which it is isolated or recombinantly produced. In one embodiment, the language "substantially free of cellular material" includes preparations of NPP1 protein, biologically active fragment or NPP1 fusion protein having less than about 30% (by dry weight) of non-NPP1 protein/fragment/fusion protein (also referred to herein as a "contaminating protein"), more preferably less than about 20% of non-NPP1 protein/fragment/fusion protein, still more preferably less than about 10% of non-NPP1 protein/fragment/fusion protein, and most preferably less than about 5% non-NPP1 protein/fragment/fusion protein. When the NPP1 protein, fusion protein, or biologically active fragment thereof is recombinantly produced, it is also preferably substantially free of culture medium, i.e., culture medium represents less than about 20%, more preferably less than about 10%, and most preferably less than about 5% of the volume of the protein preparation.

The term "low plasma PPi" as used herein refers to a level of pyrophosphate (PPi) in the plasma of a subject that is no more than 50% of the normal level of PPi for that type of subject (e.g. a human). Preferably, the level of PPi in the plasma of the subject no more than about 40%, about 30%, about 20% or about 10% of the normal level of PPi for that type of subject. Normal PPi levels for a human are reported to be 2.63±0.47 microMolar. (O'Neill et al., Nephrol Dial Transplant 2010, 25, 187-191). Pyrophosphate can be quantified enzymatically using suitable known methods, such as the uridine-diphosphoglucose (UDPG) method. (Ryan, L. M. et al., Arthritis Rheum 1979, 22, 886-91).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "subject" encompasses mammals and non-mammals. Examples of mammals include, but are not limited to, humans, chimpanzees, apes monkeys, cattle, horses, sheep, goats, swine, rabbits, dogs, cats, rats, mice, guinea pigs, and the like. Examples of non-mammals include, but are not limited to, birds, fish and the like.

As used herein, the term "therapeutically effective amount" refers to a nontoxic but sufficient amount of an agent (e.g. sNPP1 proteins) which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. The term "treating" includes the application or administration of the NPP1 proteins, fragments and fusion proteins of the invention to a subject, or application or administration of NPP1 proteins, fragments and fusion proteins of the invention to a subject who has an NPP1-associated disease or disorder or other disease or disorder associated with low levels of blood pyrophosphate, or other progressive disorder that is characterized by the accumulation of deposits of calcium and other minerals (mineralization), with the purpose of curing, healing, alleviating, relieving, altering, remedying, ameliorating, preventing, improving, or affecting the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; or improving a subject's physical or mental well-being. Treatment may be therapeutic or prophylactic. The treatment or amelioration of symptoms can be based on objective or subjective parameters; including the results of a physical examination.

Methods of Treatment

The present invention relates to uses of an isolated recombinant human soluble NPP1 ("sNPP1") which lacks an N-terminal portion (i.e., lacking cytosolic and transmembrane domains) and fusion proteins thereof for the treatment of NPP1-associated diseases and disorders. The proteins of the invention can be surprisingly used to increase NPP1 activity in vivo and increase or restore normal level of blood pyrophosphate (PPi) in subjects. The proteins of the invention can be also used to prevent accumulation of deposits of calcium in joints, kidney, heart (e.g., aorta), artery, blood vessels, or posterior longitudinal ligament of the spine.

The subject can be a human patient having deficiencies in NPP1 activity (NPP1 deficiency) exhibiting low levels of pyrophosphate, suffering from a disease or disorder associated with low levels of pyrophosphate, or suffering from a progressive disorder that is characterized by the accumulation of deposits of calcium and other minerals (mineralization) in elastic fibers. Mineralization can occur at the heart, arteries, blood vessels, the kidney, the ligaments of spine, the skin, eyes, and the digestive tract.

More specifically, the NPP1 proteins and NPP1 fusion proteins of the invention can be used to treat subjects having NPP1-associated diseases or disorders, including but not limited to, idiopathic infantile arterial calcification (IIAC), insulin resistance, hypophosphatemic rickets, and ossification of the posterior longitudinal ligament of the spine, or other diseases such as vascular calcification in chronic kidney disease (VCCKD), myocardial ischemia, joint calcification, angioid streaks, and pseudoxanthoma elasticum (PXE).

The soluble NPP1 proteins, fragment, and NPP1 fusion proteins thereof can be used to treat a wide variety of conditions in a subject. For example, treatment of conditions that can be improved by reducing and/or eliminating one or more calcification structures and/or preventing calcification structures from forming in a subject such as a mammal, for example, a human patient is within the scope of the invention.

In one particularly useful embodiment, the condition to be treated is generalized arterial calcification (also known as idiopathic arterial calcification of infancy and arterial media calcification of infancy).

In other embodiments, conditions such as pseudoxanthoma elasticum, vascular calcification in chronic kidney disease, insulin resistance, hypophosphatemic rickets, or ossification of the posterior longitudinal ligament of the spine can be also treated using the methods described herein.

Generally, the dosage of fusion protein administered to a subject will vary depending upon known factors such as age, health and weight of the recipient, type of concurrent treatment, frequency of treatment, and the like. Usually, a dosage of active ingredient (i.e., fusion protein) can be between about 0.0001 and about 50 milligrams per kilogram of body weight. Precise dosage, frequency of administration and time span of treatment can be determined by a physician skilled in the art of administration of therapeutic proteins.

A preferred embodiment of the present invention involves a method for treatment of an NPP1-associated disease or other calcification diseases which includes the step of administering a therapeutically effective amount of an isolated soluble NPP1 protein (sNPP1), biologically active fragment, or NPP1 fusion protein to a subject. As defined herein, a therapeutically effective amount of protein (i.e., an effective dosage) ranges from about 0.001 to 50 mg/kg body weight. The skilled artisan will appreciate that certain factors may influence the dosage required to effectively treat a subject, including but not limited to the severity of the disease, previous treatments, the general health and/or age of the subject, and other diseases present. Moreover, treatment of a subject with a therapeutically effective amount of protein can include a single treatment or, preferably, can include a series of treatments. It will also be appreciated that the effective dosage of protein used for treatment may increase or decrease over the course of a particular treatment.

As defined herein, a therapeutically effective amount of protein or polypeptide (i.e., an effective dosage) ranges from about 0.001 to 50 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, in the range of between about 0.1 to 20 mg/kg body weight, one time per week, twice per week, once in about 10 days, once in about 12 days, once in about 14 days, once in about 17 days, once in about 20 days, once in about 25 days, or once in about 30 days. It will also be appreciated that the effective dosage of soluble sNPP1 protein, biologically active fragment or fusion protein thereof used for the treatment may increase or decrease over the course of a particular treatment.

The invention provides for a therapeutically effective dose of sNPP1, biologically active fragment or fusion protein thereof to be administered to a patient between one time every 5 days and one time every 30 days for a period of time determined by a practitioner of skill in the art of medical sciences. In one embodiment, the period of time will be the remainder of the patient's life span. In one embodiment, the dosing frequency is between one time every 5 days and one time every 25 days. In one embodiment, the dosing frequency is between one time every 5 days and one time every 21 days. In another embodiment, the dosing frequency is between one time every 7 days and one time every 14 days. sNPP1, biologically active fragment or fusion protein thereof can be administered one time every 5 days, one time every 6 days, one time every 7 days, one time every 8 days, one time every 9 days, one time every 10 days, one time every 11 days, one time every 12 days, one time every 13 days, or one time every 14 days. In some embodiments, sNPP1, biologically active fragment or fusion protein thereof is administered about weekly. In other embodiments, sNPP1, biologically active fragment or fusion protein thereof is administered about bi-weekly. In one embodiment, the dosing frequency is one time about 30 days.

In one embodiment, the patient is less than 2 years of age. In some embodiments, about 0.1 mg, about 0.2 mg, about 0.3 mg, about 0.4 mg, about 0.5 mg, about 1 mg, about 2 mg, about 3 mg, about 5 mg, about 10 mg, about 15 mg, about 20 mg, about 25 mg, about 30 mg, about 35 mg, about 40 mg, or about 45 mg of sNPP1, biologically active fragment or fusion protein is administered to the patient with NPP1-deficiency or other calcification disease. In some embodiments, about 0.5 to about 30 mg, about 0.5 to about 20 mg, about 0.5 to about 10 mg, or about 0.5 to about 5 mg are administered to the patient.

In one embodiment, about 1 mg/kg of sNPP1, biologically active fragment or fusion protein is administered to the patient once a week. In one embodiment, about 2 mg/kg of sNPP1, biologically active fragment or fusion protein is administered to the patient once a week. In one embodiment, about 3 mg/kg of sNPP1, biologically active fragment or fusion protein is administered to the patient once a week. In one embodiment, about 4 mg/kg of sNPP1, biologically active fragment or fusion protein is administered to the patient once a week. In one embodiment, about 5 mg/kg of sNPP1, biologically active fragment or fusion protein is administered to the patient once a week. In one embodiment, about 6 mg/kg of sNPP1, biologically active fragment or fusion protein is administered to the patient once a week. In one embodiment, about 7 mg/kg of sNPP1, biologically active fragment or fusion protein is administered to the patient once a week. In one embodiment, about 8 mg/kg of sNPP1, biologically active fragment or fusion protein is administered to the patient once a week. In one embodiment, about 9 mg/kg of sNPP1, biologically active fragment or fusion protein is administered to the patient once a week. In one embodiment, about 10 mg/kg of sNPP1, biologically active fragment or fusion protein is administered to the patient once a week.

In some embodiments, the level of blood PPi in a patient prior to treatment is about 1%, about 2%, about 3%, about 5%, about 10%, about 15%, about 20%, about 30%, about 40%, about 50%, about 60%, about 70%, or about 80% of normal levels of PPi observed in a normal human individual. In one embodiment, the level of PPi in a patient prior to treatment is about 50% or less of normal levels of PPi observed in a normal human individual. In one embodiment, the level of PPi in a patient prior to treatment is about 40% or less of normal levels of PPi observed in a normal human individual. In some embodiments, the level of PPi in a patient prior to treatment is about 30% or less of normal levels of PPi observed in a normal human individual. In some embodiments, the level of PPi in a patient prior to treatment is about 30% or less of normal levels PPi observed in a normal human individual. In some embodiments, the level of PPi in a patient prior to treatment is about 20% or less of normal levels of PPi observed in a normal human individual. In some embodiments, the level of PPi in a patient prior to treatment is about 10% or less of normal levels of PPi observed in a normal human individual. In some embodiments, the level of PPi in a patient prior to treatment is about 5% or less of normal levels of PPi observed in a normal human individual. In some embodiments, a patient shows no measurable PPi prior to treatment.

sNPP1, biologically active fragment or fusion protein can be administered by, for example, subcutaneous injections, intramuscular injections, and intravenous (IV) infusions or injections.

In one embodiment, sNPP1, biologically active fragment or fusion protein is administered intravenously by IV infusion by any useful method. In one example, sNPP1, biologically active fragment or fusion protein can be administered by intravenous infusion through a peripheral line. In another example, sNPP1, biologically active fragment or fusion protein can be administered by intravenous infusion through a peripherally inserted central catheter.

In another embodiment, sNPP1, biologically active fragment or fusion protein is administered intravenously by IV injection.

In another embodiment, sNPP1, biologically active fragment or fusion protein can be administered via intraperitoneal injection.

In another embodiment, sNPP1, biologically active fragment or fusion protein can be administered by subcutaneous injections.

In another embodiment, sNPP1, biologically active fragment or fusion protein can be administered by intramuscular injections.

In still another embodiment, sNPP1, biologically active fragment or fusion protein is administered via a pharmaceutically acceptable capsule of the therapeutic protein. For example, the capsule can be an enteric-coated gelatin capsule.

In one embodiment, the method involves administering the soluble NPP1 protein or NPP1 fusion protein of the invention alone, or in combination with other agent(s). In one embodiment, the method involves administering an NPP1 protein or an NPP1 fusion protein of the invention as therapy to compensate for reduced or aberrant NPP1 expression or activity in the subject having an NPP1-deficiency or other associated disease or disorder.

In one embodiment, the isolated sNPP1 proteins, fragments, and fusion proteins can be administered before, after or concurrently with the agent or can be co-administered with other known therapies. Co-administration of the isolated sNPP1 proteins, fragments, and fusion proteins of the present invention with other therapeutic agents may provide two agents which operate via different mechanisms which yield an increased therapeutic effect. Such co-administration can solve problems due to development of resistance to drugs.

In particular aspects, this disclosure relates to a method for reducing vascular calcification in a subject in need thereof. The method is based on the surprising finding that soluble forms of NPP1 can be administered to animals that have low plasma PPi levels (an inhibitor or tissue calcification) or high serum Pi levels, to cause a transient increase in plasma PPi in the animals, and that the transient increase in plasma PPi can inhibit vascular calcification in the animal. Since the increase in plasma PPi is transient, therapy can be tailored to inhibit undesirable or pathological tissue calcification, such as vascular calcification, without inhibiting bone calcification or inducing osteomalacia.

In general terms, the disclosure relates to a method for reducing tissue calcification (e.g., vascular calcification) in a subject in need thereof, by administering to the subject two or more doses of soluble NPP1 (sNPP1). Each of the doses contains an amount of soluble NPP1 that is sufficient to achieve a transient increase in plasma PPi in the subject, preferably with a return to base-line PPi level within about 48 hours after administration of the dose. The time period between the administration of each dose is generally at least 2 days.

The subject in need thereof can be of any age and gender, and preferably has low plasma PPi or high serum Pi (e.g., resulting in an altered PPi:Pi ratio). Low plasma PPi can be due, for example, to congenital NPP1 deficiency such as mutation in the gene encoding NPP1 that lead to reduced expression of active NPP1 or reduced enzymatic activity (associated with NPP1 deficiency and autosomal-recessive hypophosphatemic rickets), and mutation in the gene encoding MRP6 that lead to absent or nonfunctional MRP6 protein (associated with pseudoxanthoma elasticum). Low plasma PPi or high serum Pi is also frequently seen in patients with chronic kidney disease, end-stage renal disease/failure, diabetes mellitus and other conditions. Accordingly, the subject in need of therapy can have chronic kidney disease (CKD), end-stage renal disease (ESRD), generalized arterial calcification of infancy (GACI), diabetes mellitus II, autosomal-recessive hypophosphatemic rickets, a cardiovascular disorder, atherosclerosis and/or pseudoxanthoma elasticum (PXE). The subject is generally a human, but can also be any other suitable mammal or non-mammal.

Tissue calcification is a progressive process and individuals born with congenital NPP1 deficiency may not show calcification of tissues for several years. By initiating therapy as early as possible, it is likely that calcification can be reduced and or minimized in such subjects. In subjects with low plasma PPi levels not caused by germ line mutation, or with high serum Pi levels (e.g., with an altered plasma PPi:Pi ratio), therapy should begin as soon as practicable (i.e., soon after the diagnosis of the conditions, such as chronic kidney disease (CKD) or end-stage renal disease (ESRD)). In certain embodiments, the subject to be treated can be between 1 month and 24 months in age, less than 1 year of age, less than 2 years of age, less than 3 years of age, less than 4 years of age, or less than 5 years of age.

Each dose of sNPP1 that is administered to the subject contains an amount of sNPP1 sufficient to achieve a transient increase in plasma PPi. Preferably, the transient increase is characterized by a peak PPi level that is at least about 40% of the normal plasma PPi level, at least about 50% of the normal plasma PPi level, at least about 60% of the normal plasma PPi level, at least about 70% of the normal plasma PPi level, at least about 80% of the normal plasma PPi level, between about 40% and 100% of the normal plasma PPi level, between about 50% and 100% of the normal plasma PPi level, between about 60% and 100% of the normal plasma PPi level, between about 70% and 100% of the normal plasma PPi level, between about 80% and 100% of the normal plasma PPi level, or between about 100% and 200% of the normal plasma PPi level.

Preferably, the transient increase in plasma PPi after administration of sNPP1 is maintained for at least about 4 hours, at least about 6 hours, at least about 8 hours, at least about 10 hours or at least about 12 hours. In addition, it is preferred that the transient increase in plasma PPi returns to the subject's base-line PPi level within about 48 hours after administration of the dose, within about 3 days after administration of the dose or within about 4 days after administration of the dose.

The low plasma PPi in a subject prior to treatment is about 50% or less, preferably 40% or less of normal levels of PPi observed in a normal subject (e.g., a human). In some aspects, the level of PPi in a subject prior to treatment is about 30% or less of normal levels of PPi. In other aspects, the level of PPi in a subject prior to treatment is about 20% or less of normal levels of PPi. In some other aspects, the level of PPi in a subject prior to treatment is about 10% or less of normal levels. In some aspects, a subject may have no measurable PPi prior to treatment.

The high serum Pi in a subject prior to treatment is about 110% or more, preferably 125% or more of normal levels of Pi observed in a normal subject (e.g., a human). In some aspects, the level of Pi in a subject prior to treatment is about 150% or more of normal levels of PPi. In other aspects, the level of Pi in a subject prior to treatment is about 200% or more of normal levels of PPi. In some other aspects, the level of Pi in a subject prior to treatment is about 300% or more of normal levels. Without wishing to be bound by any particular theory, it is believed that inducing a transient increase in serum PPi can compensate for elevated plasma Pi levels and transiently restore normal or nearly normal PPi:Pi ratio, thereby inhibiting tissue calcification which is promoted by higher than normal levels of serum Pi.

The amount of sNPP1 sufficient to achieve the transient increase in plasma PPi can be easily determined by a clinician of ordinary skill, for example, by administering a dose that is expected to produce the transient increase in plasma PPi, determining whether the transient increase occurs and then making appropriate adjustments to the dose. The amount to administer will be influenced by a number of conventional factors, including the particular sNPP1 used, the age, health and weight of the subject, the subject's sensitivity to drugs, and other relevant factors. Typically, the amount of sNPP1 to be administered in each dose is between about 0.001 and about 50 milligrams per kilogram of body weight, with 1 mg/kg to 5 mg/kg, 1 mg/kg to 10 mg/kg, 1 mg/kg to 20 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg being preferred. Precise dosage, frequency of administration and time span of treatment can be determined by a physician skilled in the art of administration of therapeutic proteins.

In some preferred embodiments, each dose contains about 1.0 mg to about 5.0 mg sNPP1 per Kg body weight, about 1.0 mg to about 10.0 mg sNPP1 per Kg body weight or about 1.0 mg to about 20.0 mg sNPP1 per Kg body weight.

The time period between doses is selected to permit the subject's serum PPi levels to return to base-line levels, and is at least 2 (48 hours) days, but can be longer as desired or indicated. For example, the time period between doses can be 3 days, 4 days, 5 days, 6 days, one week, 10 days, 12 days, two weeks, three weeks or about 1 month.

In general, it is desirable to initiate the therapy according to the methods described herein as soon as practicable after diagnosis of low plasma PPi, high serum Pi, or NPP1 deficiency. Subjects born with congenital NPP1 deficiency may not show calcification of tissues for several years. By initiating therapy as early as possible, it is likely that calcification can be reduced and or minimized in such subjects. In subjects with low plasma PPi levels not caused by germ line mutation or with high serum Pi, therapy should begin as soon as practicable after the diagnosis of conditions, such as chronic kidney disease (CKD) or end-stage renal disease (ESRD).

The method provides an effective way to reduce tissue calcification (e.g. vascular calcification) in a subject with low plasma PPi or with high serum Pi, including those with an altered ratio of PPi to Pi. The tissue calcification is preferably vascular calcification, which is preferably arterial calcification but can also be venus calcification. The vascular calcification can be intimal or medial. The subject to be treated in accordance with the methods described herein can have NPP1 deficiency, generalized arterial calcification (GACI), also known as idiopathic arterial calcification of infancy and arterial media calcification of infancy. The subject to be treated can also have a cardiovascular disorder, such as coronary artery disease and/or atherosclerosis. The subject to be treated can have chronic kidney disease (CKD) or end-stage renal disease (ESRD). The subject to be treated can have diabetes mellitus (e.g. type II diabetes). The subject to be treated can have pseudoxanthoma elasticum (PXE).

The sNPP1 can be administered by any suitable method or route of administration, such as parenterally, orally or by inhalation. Parenteral administration, such as, intravenous injection or infusion, subcutaneous injection, intraperitoneal injections, or intramuscular injections is preferred.

If desired, the sNPP1 can be administered with one or more co-therapeutic agents. For co-therapy the sNPP1 and one or more additional therapeutic agents are administered so that there is substantial overlap in their individual pharmacological activities in the subject. Accordingly, any co-therapeutic agent can be administered prior to, concurrently with or subsequent to the administration of sNPP1. Co-therapy may provide two agents which operate via different mechanisms which yield an increased therapeutic effect.

In addition to causing a transient increase in serum PPi, it is believed that administering sNPP1 in accordance with the methods described herein, can alter the levels of certain proteins in the subject. For example, without wishing to be bound by any particular theory, it is believed that administering sNPP1 in accordance with the methods described herein can decrease the levels of osteopontin, osteoprotegerin and fibroblast growth factor 23 (FGF-23) in the subject. The levels of these proteins can therefor also be used, in addition to plasma PPi and serum Pi levels, to monitor therapy and tailor dosing.

sNPP1

The present invention employes soluble NPP1 that a biologically active NPP1 domain of NPP1 (i.e., NPP1 components that contain at least one extracellular catalytic domain of naturally occurring NPP1 for the pyrophosphatase and/or phosphodiesterase activity). The soluble NPP1 proteins of the invention comprise at least the NPP1 domain essential to carry out the pyrophosphatase and/or phosphodiesterase activity.

In one embodiment, the soluble NPP1, fragment, and fusion proteins thereof can form functional homodimers or monomer. In a preferred embodiment, a soluble NPP1 protein or NPP1 fusion protein thereof can be assayed for pyrophosphatase activity as well as the ability to increase pyrophosphate levels in vivo.

Preferred soluble NPP1 proteins and NPP1 fusion proteins of the invention are enzymatically active in vivo (e.g., human). In one embodiment, the soluble protein comprises amino acid sequence having at least 60, 70, 75, 80, 85, 90, 91, 92, 93, 94, 95, 96, 97, 98, 99% sequence identity to the following sequence:

(SEQ ID NO: 2)

```
PSCAKEVKSCKGRCFERTFGNCRCDAACVELGNCCLDYQETCIEPEH

IWTCNKFRCGEKRLTRSLCACSDDCKDKGDCCINYSSVCQGEKSWVE

EPCESINEPQCPAGFETPPTLLFSLDGFRAEYLHTWGGLLPVISKLK
```

-continued

KCGTYTKNMRPVYPTKTFPNHYSIVTGLYPESHGIIDNKMYDPKMNA

SFSLKSKEKFNPEWYKGEPIWVTAKYQGLKSGTFFWPGSDVEINGIF

PDIYKMYNGSVPFEERILAVLQWLQLPKDERPHFYTLYLEEPDSSGH

SYGPVSSEVIKALQRVDGMVGMLMDGLKELNLHRCLNLILISDHGME

QGSCKKYIYLNKYLGDVKNIKVIYGPAARLRPSDVPDKYYSFNYEGI

ARNLSCREPNQHFKPYLKHFLPKRLHFAKSDRIEPLTFYLDPQWQLA

LNPSERKYCGSGFHGSDNVFSNMQALFVGYGPGFKHGIEADTFENIE

VYNLMCDLLNLTPAPNNGTHGSLNHLLKNPVYTPKHPKEVHPLVQCP

FTRNPRDNLGCSCNPSILPIEDFQTQFNLTVAEEKIIKHETLPYGRP

RVLQKENTICLLSQHQFMSGYSQDILMPLWTSYTVDRNDSFSTEDFS

NCLYQDFRIPLSPVHKCSFYKNNTKVSYGFLSPPQLNKNSSGIYSEA

LLTTNIVPMYQSFQVIWRYFHDTLLRKYAEERNGVNVVSGPVFDFDY

DGRCDSLENLRQKRRVIRNQEILIPTHFFIVLTSCKDTSQTPLHCEN

LDTLAFILPHRTDNSESCVHGKHDSSWVEELLMLHRARITDVEHITG

LSFYQQRKEPVSDILKLKTHLPTFSQED

Any desired enzymatically active form of soluble NPP1 can be used in the methods described herein. The enzymatically active sNPP1 can increase PPi levels in suitable enzymatic assays, and can be assayed for pyrophosphatase activity, phosphodiesterase activity, or pyrophosphatase and phosphodiesterase activity. Typically, the sNPP1 contains at least an NPP1 component that lacks the N-terminal cytosolic and transmembrane domains of naturally occurring transmembrane NPP1. In preferred aspects, the NPP1 component contains the cysteine-rich region (amino acids 99-204 of SEQ ID NO:1) and the catalytic region (amino acids 205-591 of SEQ ID NO:1) of naturally occurring human NPP1. Typically, the NPP1 component also includes the C-terminal region (amino acids 592 to 925 of SEQ ID NO:1), and has the amino acid sequence of SEQ ID NO:2. However, the C-terminal region can be truncated if desired. Accordingly, preferred NPP1 components include the cysteine-rich region and catalytic region of human NPP1 (amino acids 99-591 of SEQ ID NO:1) or the cysteine-rich region, the catalytic region and the C-terminal region of human NPP1 (SEQ ID NO:2). Other preferred NPP1 components contain only a portion of the cysteine-rich domain and have the sequence of amino acids 107 to 925 of SEQ ID NO:1 or amino acids 187 to 925 of SEQ ID NO:1.

The cysteine rich region of NPP1 (i.e., amino acids 99 to 204 of SEQ ID NO: 1) can facilitate dimerization of the sNPP1. The sNPP1, including fusion proteins, can be in the form of a monomer of functional homodimer.

The amino acid sequence of the NPP1 component can be a variant of the naturally occurring NPP1 sequence, provided that the NPP1 component is enzymatically active. NPP1 variants are enzymatically active and have at least 80%, at least 85%, at least 90%, at least 95% and more preferably at least 96% amino acid sequence identity to the corresponding portion of human NPP1 (e.g., over the length of the cysteine-rich region, the catalytic region, the c-terminal region, the cysteine-rich region plus the catalytic region, the cystein-rich region plus the catalytic region plus the c-terminal region. Preferred NPP1 variants have at least 90%, preferably at least 95%, more preferably at least 97% amino acid sequence identity to (i) the amino acid sequence of residues 205-591 of SEQ ID NO: 1, (ii) the amino acid sequence of residues 99-591 of SEQ ID NO:1, (iii) the amino acid sequence of residues 99-925 of SEQ ID NO:1, (iv) the amino acid sequence of residues 107-925 of SEQ ID NO:1, or (v) the amino acid sequence of residues 187-925 of SEQ ID NO:1. Suitable positions for amino acid variation are well-known from NPP1 structural studies and analysis of disease-associated mutations in NPP1. For example, substitution of the following amino acids occurs in certain disease-associated mutations that reduce NPP1 enzymatic activity, and variations of the amino acids at these positions should be avoided: Ser216, Gly242, Pro250, Gly266, Pro305, Arg349, Tyr371, Arg456, Tyr471, His500, Ser504, Tyr513, Asp538, Tyr570, Lys579, Gly586; Tyr659, Glu668, Cys726, Arg774, His777, Asn792, Asp804, Arg821, Arg888, and Tyr901. (See, e.g., Jansen, S. et al., Structure 20:1948-1959 (2012).)

In one embodiment, the soluble NPP1 protein can be a fusion protein recombinantly fused or chemically bonded (e.g., covalent bond, ionic bond, hydrophobic bond and Van der Waals force) to a fusion partner. In another embodiment, the fusion protein has at least 70, 75, 80, 85, 90, 91, 92, 93, 94, 95, 96, 97, 98, or 99% sequence identity to SEQ ID NO:3 or SEQ ID NO:4.

To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., sNPP1 amino acid sequence of SEQ ID NO:2; amino acids 107-925 of SEQ ID NO:1 or amino acids 187-925 of SEQ ID NO:1). The amino acid residues or nucleotides at corresponding amino acid positions are then compared. When a position in the first sequence is occupied by the same amino acid residue or nucleotide as the corresponding position in the second sequence, then the molecules are identical at that position (as used herein amino acid is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J Mol Biol 1970, 48, 444-453) algorithm which has been incorporated into the GAP program in the GCG software package (available at www.gcg.com), using either a Blosum 62 matrix or a PAM250 matrix, and a gap weight of 16, 14, 12, 10, 8, 6, or 4 and a length weight of 1, 2, 3, 4, 5, or 6. In another embodiment, the percent identity between two amino acid is determined using the algorithm of E. Meyers and W. Miller (CABIOS, 1989, 4, 11-17) which has been incorporated into the ALIGN program (version 2.0 or 2.0U), using a PAM120 weight residue table, a gap length penalty of 12 and a gap penalty of 4.

The sNPP1 can consist of or consist essentially of an NPP1 component as described herein. Alternatively, the sNPP1 can be in the form of a fusion protein that contains an NPP1 component and one or more other polypeptides, referred to as fusion partners, optionally through a suitable linker in each instance, or in the form of a conjugate between an NPP1 component and another molecule (e.g., PEG). When the sNPP1 is in the form of a fusion protein, each fusion partner is preferably located c-terminally to the NPP1 component. Without wishing to be bound by any particular theory, it is believed that fusion proteins that contain an NPP1 component that contains the cysteine-rich region and catalytic region, and one or more fusion proteins that are located c-terminally to the NPP1 component, are preferred over other configurations of NPP1 fusion proteins because they can be expressed at sufficient levels and are sufficiently stable to be used as therapeutic proteins.

Any suitable fusion partner can be included in the fusion protein. Advantageously, a number of fusion partners are well-known in the art that can provide certain advantages, such as reduced aggregation and immunogenicity, increased the solubility, improved expression and/or stability, and improved pharmacokinetic and/or pharmacodynamics performance. See, e.g., Strohl, W. R. BioDrugs 29:215-239 (2015). For example, it is well-known that albumin, albumin fragments or albumin variants (e.g., human serum albumin and fragments or variants thereof) can be incorporated into fusion proteins and that such fusion proteins can be easily purified, stable and have an improved plasma half-life. Suitable albumin, albumin fragments and albumin variants that can be used in the sNPP1 fusion proteins are disclosed, for example in WO 2005/077042A2 and WO 03/076567A2, each of which is incorporated herein by reference in its entirety. Fusions to human transferrin are also known to improve half-life. See, e.g., Kim B J et al., J Pharmacol Expr Ther 334(3):682-692 (2010); and WO 2000/020746. Peptides that bind to albumin or transferrin, such as antibodies or antibody fragments, can also be used. See, e.g., EP 0486525 B1, U.S. Pat. No. 6,267,964 B1, WO 04/001064A2, WO 02/076489A1, WO 01/45746, WO 2006/004603, and WO 2008/028977. Similarly immunoglobulin Fc fusion proteins are well-known. See, e.g., Czajkowsky D M et al., EMBO Mol Med 4(10):1015-1028 (2012), U.S. Pat. Nos. 7,902,151; and 7,858,297, the entire teachings of which are incorporated herein by reference in their entirety. The fusion protein can also include a CTP sequence (see also, Fares et al., Endocrinol 2010, 151, 4410-4417; Fares et al., Proc Natl Acad Sci 1992, 89, 4304-4308; and Furuhashi et al., Mol Endocrinol 1995, 9, 54-63). Preferably, the fusion partner is the Fc of an immunoglobulin (e.g., Fc or human IgG1). The Fc can include CH1, CH2 and CH3 of human IgG1, and optionally the human IgG1 hinge region (EPKSCDKTHTCPPCP (SEQ ID NO:13)) or a portion of the human IgG1 hinge region (e.g., DKTHTCPPCP (SEQ ID NO:14) or PKSCDKTHTCPPCP (SEQ ID NO:15)) if desired. In some fusion proteins, the Fc can include CH2 and CH3 of human IgG1, or the Fc of human IgG2 or human IgG4, if desired.

Preferably, the sNPP1 fusion protein comprises an NPP1 component and a peptide that increases the half-life of the fusion protein, most preferably the Fc of an immunoglobulin (e.g., Fc or human IgG1). As used herein, a "protein that increases the half-life of the fusion protein" refers to a protein that, when fused to a soluble NPP1 or biologically active fragment, increases the half-life of the soluble NPP1 polypeptide or biologically active fragment as compared to the half-life of the soluble NPP1 polypeptide, alone, or the NPP1 biologically active fragment, alone.

In one embodiment, the half-life of the NPP1 fusion protein is increased 50% as compared to the half-life of the NPP1 polypeptide or biologically active fragment, alone. In another embodiment, the half-life of the NPP1 fusion protein is increased 60% as compared to the half-life of the NPP1 polypeptide or biologically active fragment, alone. In another embodiment, the half-life of the NPP1 fusion protein is increased 70% as compared to the half-life of the NPP1 polypeptide or biologically active fragment, alone. In another embodiment, the half-life of the NPP1 fusion protein is increased 80% as compared to the half-life of the NPP1 polypeptide or biologically active fragment, alone. In another embodiment, the half-life of the NPP1 fusion protein is increased 90% as compared to the half-life of the NPP1 polypeptide or biologically active fragment, alone.

In another embodiment, the half-life of the NPP1 fusion protein is increased 2 fold, 3 fold, 4 fold, 5 fold, 6 fold, 7 fold, 8 fold, 9 fold, or 10 fold as compared to the half-life of the NPP1 polypeptide or biologically active fragment, alone. Methods for determining the half-life of a protein or fusion protein are well known in the art. For example, Zhou et al., Determining Protein Half-Lives, Methods in Molecular Biology 2004, 284, 67-77 discloses numerous methods for testing of the half-life of a protein. If desired, the fusion protein can be conjugated to polymers or other suitable compounds that extend half-life, such as polyethylene glycol (PEG), can be conjugated to the NPP1 fusion proteins.

In one embodiment, the peptide which increases the half-life of the fusion protein is a CTP sequence (see also, Fares et al., 2010, Endocrinol., 151(9):4410-4417; Fares et al., 1992, Proc. Natl. Acad. Sci, 89(10):4304-4308; and Furuhashi et al., 1995, Molec. Endocrinol., 9(1):54-63).

In another embodiment, the peptide which increases the half-life of the fusion protein is an Fc domain of an Ig.

Fusion partners may also be selected to target the fusion protein to desired sites of clinical or biological importance (e.g., site of calcification). For example, peptides that have high affinity to the bone are described in U.S. Pat. No. 7,323,542, the entire teachings of which are incorporated herein by reference. Peptides that can increase protein targeting to calcification sites can contain a consecutive stretch of at least about 4 acidic amino acids, for example, glutamic acids or aspartic acids. Typically, the peptide that targets the fusion protein to calcification sites will comprise between 4 and 20 consecutive acidic amino acids, for example 4, 5, 6, 7, 8, 9, 10, 11, 12, 13, 14, 15, 16, 17, 18, 19 or 20 consecutive amino acids selected from glutamic acid and aspartic acid. The peptide can consist solely of glutamic acid residues, solely of aspartic acid residues, or be a mixture of glutamic acid and aspartic acid residues. A particularly preferred moiety for targeting to sights of calcification is $Asp_{10}$ (SEQ ID NO:18).

In one embodiment, the NPP1 fusion protein of the invention comprises an NPP1 polypeptide and a moiety that increase protein targeting to calcification sites such as a consecutive stretch of acidic amino acids, for example, glutamic acids or aspartic acids.

Suitable peptide linkers for use in fusion proteins are well-known and typically adopt a flexible extended conformation and do not interfere with the function of the NPP1 component or the fusion partners. Peptide linker sequences may contain Gly, His, Asn and Ser residues in any combination. The useful peptide linkers include, without limitation, poly-Gly, poly-His, poly-Asn, or poly-Ser. Other near neutral amino acids, such as Thr and Ala can be also used in the linker sequence. Amino acid sequences which can be usefully employed as linkers include those disclosed in Maratea et al., Gene 1985, 40, 39-46; Murphy et al., Proc Natl Acad Sci USA 1986, 83, 8258-8262; U.S. Pat. Nos. 4,935,233 and 4,751,180. Other suitable linkers can be obtained from naturally occurring proteins, such as the hinge region of an immunoglobulin. A preferred synthetic linker is $(Gly_4Ser)_n$, where n is 1, 2, 3, 4, 5, 6, 7, 8, 9 or 10 (SEQ ID NO:19). Preferably, n is 3 or 4. For example, in some embodiments the linker is $(Gly_4Ser)_3$ (SEQ ID NO:16) and the fusion protein include a linker with the amino acid sequence GlyGlyGlyGlySerGlyGlyGlyGlySerGlyGlyGlyGlySer (SEQ ID NO:16). Typically, the linker is from 1 to about 50 amino acid residues in length, or 1 to about 25 amino acids in length. Frequently, the linker is between about 8 and about 20 amino acids in length.

Preferred NPP1 fusion proteins comprise from N-terminus to C-terminus an NPP1 component, optionally a linker, an Fc region of an immunoglobulin (e.g., human IgG1 Fc optionally including hinge or a portion thereof), optionally a second liner, and optionally a targeting moiety. Thus, the Fc region and the optional targeting moiety, when present, are each located C-terminally to the NPP1 component. The NPP1 component preferably comprises the cysteine-rich region and the catalytic domain of NPP1, lacks the N-terminal cytosolic and transmembrane domains, and optionally contains the C-terminal region.

A preferred fusion protein comprises, from N-terminus to C-terminus, an NPP1 component comprising the cysteine-rich domain, the catalytic domain and the C-terminal region of human NPP1; and the Fc region, including hinge, of a human immunoglobulin. Preferably, the Fc region is from human IgG1. In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:3. A preferred fusion protein of this type has the amino acid sequence of SEQ ID NO:3.

Another preferred fusion protein comprises, from N-terminus to C-terminus, an NPP1 component comprising the cysteine-rich domain, the catalytic domain and the C-terminal region of human NPP1; a linker (e.g., $(Gly_4Ser)_3$ (SEQ ID NO:16)); and the Fc region, including hinge, of a human immunoglobulin. Preferably, the Fc region is from human IgG1.

Another preferred fusion protein comprises, from N-terminus to C-terminus, an NPP1 component comprising the cysteine-rich domain, the catalytic domain and the c-terminal region of human NPP1; the Fc region, including hinge or a portion thereof, of a human immunoglobulin; and a moiety targeting the fusion protein to sites of calcification. Preferably, the Fc region is from human IgG1. Preferably, the moiety targeting the fusion protein to sites of calcification is $Asp_{10}$ (SEQ ID NO:18). More preferably, the Fc region is from human IgG1 and the moiety targeting the fusion protein to sites of calcification is $Asp_{10}$ (SEQ ID NO:18). In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:4. A preferred fusion protein of this type has the amino acid sequence of SEQ ID NO:4.

Another preferred fusion protein comprises, from N-terminus to C-terminus, an NPP1 component comprising the cysteine-rich domain, the catalytic domain and the c-terminal region of human NPP1; a linker (e.g., $(Gly_4Ser)_3$ (SEQ ID NO:16)); the Fc region, including hinge or a portion thereof, of a human immunoglobulin; and a moiety targeting the fusion protein to sites of calcification. Preferably, the Fc region is from human IgG1. Preferably, the moiety targeting the fusion protein to sites of calcification is $Asp_{10}$ (SEQ ID NO:18). More preferably, the Fc region is from human IgG1 and the moiety targeting the fusion protein to sites of calcification is $Asp_{10}$ (SEQ ID NO:18).

Another preferred fusion protein comprises, from N-terminus to C-terminus, an NPP1 component comprising a portion of the cysteine-rich domain, the catalytic domain and the c-terminal region of human NPP1; optionally a linker (e.g., $(Gly_4Ser)_3$ (SEQ ID NO:16)); the Fc region, including hinge or a portion thereof, of a human immunoglobulin. Preferably, the Fc region is from human IgG1. In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:9, SEQ ID NO:10, SEQ ID NO:11, or SEQ ID NO:12. Preferred fusion protein of this type have the amino acid sequence of SEQ ID NO:9, SEQ ID NO:10, SEQ ID NO:11 or SEQ ID NO:12.

In particularly preferred aspects, a fusion protein of SEQ ID NO:3 is administered in accordance with the methods described herein. In other particularly preferred aspect, a fusion protein of SEQ ID NO:4 is administered in accordance with in the methods described herein. In other particularly preferred aspect, a fusion protein of SEQ ID NO:9 is administered in accordance with in the methods described herein. In other particularly preferred aspect, a fusion protein of SEQ ID NO:10 is administered in accordance with the methods described herein. In other particularly preferred aspect, a fusion protein of SEQ ID NO:11 is administered in accordance with the methods described herein. In other particularly preferred aspect, a fusion protein of SEQ ID NO:12 is administered in accordance with the methods described herein.

Fusion proteins of the present invention can be prepared using standard methods, including recombinant techniques or chemical conjugation well known in the art. Techniques useful for isolating and characterizing the nucleic acids and proteins of the present invention are well known to those of skill in the art and standard molecular biology and biochemical manuals can be consulted to select suitable protocols for use without undue experimentation. See, for example, Sambrook et al., 1989, "Molecular Cloning: A Laboratory Manual", $2^{nd}$ ed., Cold Spring Harbor, the content of which is herein incorporated by reference in its entirety.

The isolated recombinant human sNPP1, fragment, and fusion proteins thereof, can be produced in any useful protein expression system including, without limitation, cell culture (e.g., CHO cells, COS cells, HEK203), bacteria such as Escherichia coli (E. coli) and transgenic animals, including, but no limited to, mammals and avians (e.g., chickens, quail, duck and turkey). For expression, a construct that encodes the sNPP1 and includes a suitable signal sequence (e.g, from human Ig heavy chain, NPP2, NPP4, NPP7 or human serum albumin, for example) in frame with the sequence of the sNPP1 and operably linked to suitable expression control elements.

The sNPP1, including the fusion proteins, and physiologically acceptable salt forms thereof are typically formulated into a pharmaceutical composition for administration in accordance with the methods described herein. Pharmaceutical compositions typically include a pharmaceutically acceptable carrier or excipient. Compositions comprising such carriers, including composite molecules, are formulated by well-known conventional methods (see, for example, Remington's Pharmaceutical Sciences, $14^{th}$ ed., Mack Publishing Co., Easton, Pa.), the entire teachings of which are incorporated herein by reference. The carrier may comprise a diluent. In one embodiment, the pharmaceutical carrier can be a liquid and the fusion protein may be in the form of a solution. The pharmaceutical carrier can be wax, fat, or alcohol. In another embodiment, the pharmaceutically acceptable carrier may be a solid in the form of a powder, a lyophilized powder, or a tablet. In one embodiment, the carrier may comprise a liposome or a microcapsule. The pharmaceutical compositions can be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized protein generally has increased stability and a longer shelf life than a liquid solution of the protein.

EXAMPLES

The present invention is further exemplified by the following examples. The examples are for illustrative purpose only and are not intended, nor should they be construed as limiting the invention in any manner.

Methods

Animals:

Six week old wildtype male C57B1/6J mice were used. The average weight of these mice ranged from 21-22 g. Mice were dosed with sNPP1-Fc [1.04 mg/ml] or sNPP1-Fc-D10 [1.03 mg/ml] by subcutaneous (SC) or intravenous (IV) injection at a concentration of 5 mg/kg. Table 1.

TABLE 1

| ID | Drug/Route | Time (h) |
|---|---|---|
| 1 | No treatment | 0 |
| 2 | No treatment | 0 |
| 3 | sNPPI-Fc/IV | 1 |
| 4 | sNPPI-Fc/IV | 1 |
| 5 | sNPPI-FcD10/IV | 1 |
| 6 | sNPPI-FcD10/IV | 1 |
| 7 | sNPPI-Fc/SC | 4 |
| 8 | sNPPI-Fc/SC | 4 |
| 9 | sNPPI-FcD10/SC | 4 |
| 10 | sNPPI-FcD10/SC | 4 |

Two different strains of mice lacking NPP1 were used. Enpp1$^{-/-}$ mice were previously described in Lomashvili, K. A. et al., Kidney Int 2014, 85, 1351-1356. To accelerate arterial calcification, the diet was supplemented with 1.5% phosphate (final phosphorus content: 2%) using a mixture of $NaH_2PO_4$ and $Na_2HPO_4$ in proportions to yield a neutral pH as previously described. (O'Neill, W. C. et al., Kidney Int 2011, 79, 512-517).

Chronic Kidney Disease (CKD) model: Wild-type sprague dawley rats were used in CKD model studies. The rats were fed a diet containing 0.25-0.75% adenine and high levels of phosphorus (0.75-0.9% phosphorus versus 0.4% in normal chow). The excess dietary adenine saturates the normal adenine phosphoribosyltransferase salvage pathway and is instead metabolized to 2,8-dihydroxyadenine, which precipitates and forms crystals in the kidney tubules due to its low solubility. These crystals cause tubular injury, inflammation, obstruction, and fibrosis in the kidneys and lead to a phenotype consistent with human CKD. The resulting kidney damage and renal failure leads to impaired phosphate excretion resulting in abnormally high serum Pi levels and disordered mineral metabolism, such as general calcification of soft tissues. The high level of phosphorus in the diet accelerates arterial calcification. Rats on the high adenine diet develop uremia, hyperphosphatemia, secondary hyperparathyroidism, renal osteodystrophy, and vascular calcification.

Plasma Preparation:

Blood was collected by cardiac puncture and immediately mixed (9:1 vol:vol blood to 110 mM citric acid solution). Serum collection results in release of excess pyrophosphate (PPi) from platelets, and EDTA inhibition of clotting may interfere with the assay. The tubes of citrated blood were nutated for several minutes and then spun at 2,000×g for 10-15 min. The top layer of plasma was collected (100-300 μl) and approximately 200 μl was added to a 10 kDa centricon. These tubes are then spun at 12,000×g for 10 min to deproteinize the plasma. After the spin, the flow-through liquid was collected into a new tube. The plasma and deproteinized samples are frozen at −20° C. until analysis.

Fluorometric PPi Assay:

This assay employs a fluorogenic PPi sensor that has its fluorescence intensity proportionally dependent upon the PPi concentration. 10 kDa filtered samples (4 μl) was added to 46 μl of assay buffer. PPi sensor stock solution (200×) was diluted in assay buffer and 50 μl of this was added to the sample. After room temperature incubation for 20 min, the solid black 96-well plate was read for fluorescence (Ex/Em=316/456 nm).

Assays:

NPP1 activity was measured as previously described. (Villa-Bellosta, R. et al., Am J Physiol Heart Circ Physiol 2011, 301, H61-H68). Briefly, plasma was added to 20 volumes of physiologic buffer containing 200 nM ATP and 1.5 uCi [32P] ATP/ml for 10 minutes at 37° C. The reaction was then separated by thin-layer chromatography on polyethyleneimine cellulose and the amount of PPi produced was determined by densitometry of autoradiograms. Plasma PPi was measured as previously described (Lomashvili, K. A. et al., Kidney Int 2014, 85, 1351-1356), using plasma freshly filtered through a 30 kD cut-off filter and an enzyme assay based on the conversion of PPi and UDP-glucose to UTP and glucose-1-phosphate by UDPglucose pyrophosphorylase. All water used was pretreated with hydroxyapatite to remove contaminating PPi. Aortic calcium was measured calorimetrically in HCl acid extracts of dried aortas as previously described. (Lomashvili, K. A. et al., Kidney Int 2014, 85, 1351-1356). Calcium content was normalized to dry weight and fractional reductions in calcification were determined after subtracting the calcium content of normal mouse aortas.

Blood Cell Fractionation:

To prepare leukocytes and platelets, freshly drawn, heparinized human blood was centrifuged at 250 g for 15 minutes at room temperature. The plasma was removed and centrifuged at 2200 g for 12 minutes to obtain platelets. The pellet from the first centrifugation was re-suspended in normal saline to the original blood volume and 4 volumes of lysis buffer (155 mmol/L ammonium chloride; 10 mmol/L sodium bicarbonate; 0.1 mmol/L EDTA, pH 7.4) was added on ice for 5-10 minutes. This was repeated after centrifugation and removal of the supernatant, yielding purified leukocytes after a final centrifugation.

Statistical Analysis:

Continuous variables are expressed as means±standard errors with differences determined by Student's t-test. Aortic calcium content was analyzed after logarithmic transformation.

Example I

Background:

The experiment was conducted to determine whether there is an increase in PPi levels of wild-type mice that are dosed with variants of sNPP1. For this, 1 hour time point was selected for a single intravenous injection therapy and 4 hour time point for single subcutaneous injection therapy. The estimation of PPi levels was determined by the abcam PPi fluorometric assay.

Results:

The raw data from 1 min reads (9 total reads) were averaged and converted to % of normal plasma (WT). Table 2

TABLE 2

| | Blank | Blank | Buffer | Buffer | WT1 | WT2 | IV Fc-1 | IV Fc-2 | IV D10-1 | IV D10-2 | sc Fc-1 | sc Fc-2 | sc D10-1 | sc D10-2 |
|---|---|---|---|---|---|---|---|---|---|---|---|---|---|---|
| 1 | 0.4 | 0.4 | 32.6 | 31.1 | 36.2 | 40.2 | 37.9 | 48.0 | 51.0 | 40.6 | 47.0 | 45.9 | 46.3 | 47.3 |
| 2 | 0.4 | 0.4 | 31.5 | 30.1 | 36.3 | 40.8 | 37.2 | 46.7 | 50.8 | 39.0 | 46.5 | 44.6 | 46.7 | 47.3 |
| 3 | 0.4 | 0.4 | 31.5 | 31.1 | 35.5 | 40.8 | 37.0 | 45.7 | 51.0 | 38.8 | 46.2 | 44.1 | 46.0 | 46.2 |
| 4 | 0.4 | 0.4 | 31.1 | 31.3 | 35.5 | 40.4 | 37.0 | 46.0 | 49.5 | 38.8 | 46.6 | 45.3 | 45.6 | 46.2 |
| 5 | 0.4 | 0.4 | 31.2 | 29.9 | 35.5 | 39.7 | 35.4 | 45.7 | 50.3 | 38.6 | 46.3 | 43.7 | 46.4 | 46.4 |
| 6 | 0.3 | 0.4 | 31.0 | 29.8 | 35.4 | 40.2 | 36.0 | 44.7 | 50.9 | 39.0 | 45.7 | 44.2 | 44.4 | 44.8 |
| 7 | 0.4 | 0.4 | 30.7 | 31.2 | 34.2 | 39.6 | 35.1 | 45.5 | 50.9 | 38.6 | 45.8 | 43.5 | 45.5 | 45.7 |
| 8 | 0.4 | 0.4 | 32.0 | 29.4 | 34.9 | 40.8 | 35.5 | 45.4 | 50.4 | 37.7 | 45.0 | 43.6 | 46.1 | 44.5 |
| 9 | 0.4 | 0.3 | 31.0 | 29.6 | 34.3 | 38.9 | 35.6 | 45.3 | 51.3 | 37.1 | 45.7 | 43.4 | 44.8 | 45.1 |
| ave | 0.4 | 0.4 | 31.4 | 30.4 | 35.3 | 40.1 | 36.3 | 45.9 | 50.7 | 38.7 | 46.1 | 44.2 | 45.7 | 45.9 |

Intravenous or subcutaneous injection of sNPP1 protein variants (5 mg/kg) in the wild-type mice shows an increase of PPi concentration above normal plasma levels as shown in FIG. 5. FIG. 5 illustrates pyrophosphate level in blood in wild-type mice after administration of sNPP1-Fc or sNPP1-Fc-D10 intravenously (1 hour post injection) and subcutaneously (4 hour post injection).

Example II

Figure 6:
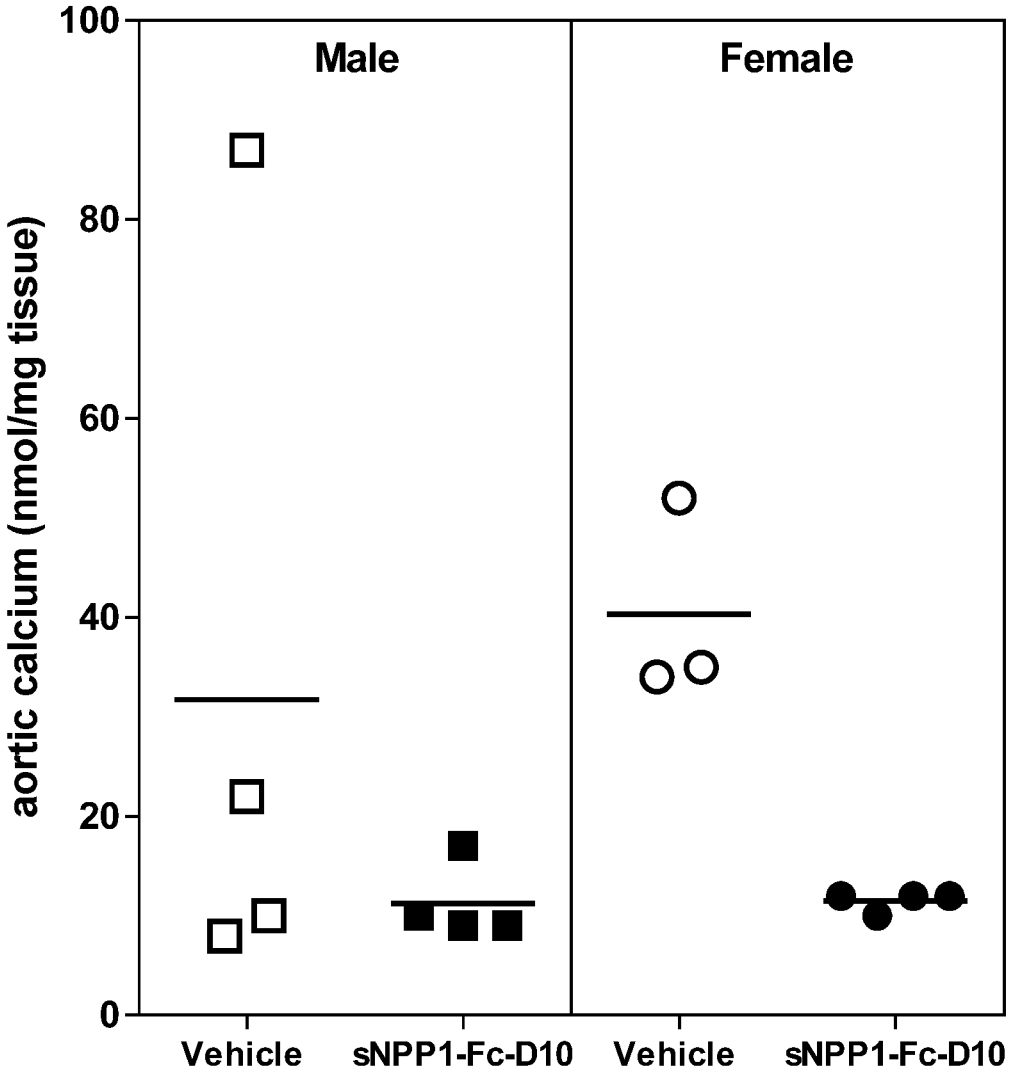
FIG. 6 illustrates prevention of aortic calcification in Enpp1(−/−) mice with sNPP1-Fc-D10 treatment. Enpp1 (−/−) mice were treated subcutaneously with vehicle or 6 mg/kg sNPP1-Fc-D10 every other day over a period of 21 days. Aortic calcium levels are shown for males and females.

Enpp1(−/−) knock-out mice were treated subcutaneously with vehicle or 6 mg/kg sNPP1-Fc-D10 every other day over a period of 21 days. Aortic calcium levels are shown for males and females. FIG. 6 shows effective prevention of aortic calcification in Enpp1(−/−) mice with sNPP1-Fc-D10 treatment.

Example III

Figure 7:
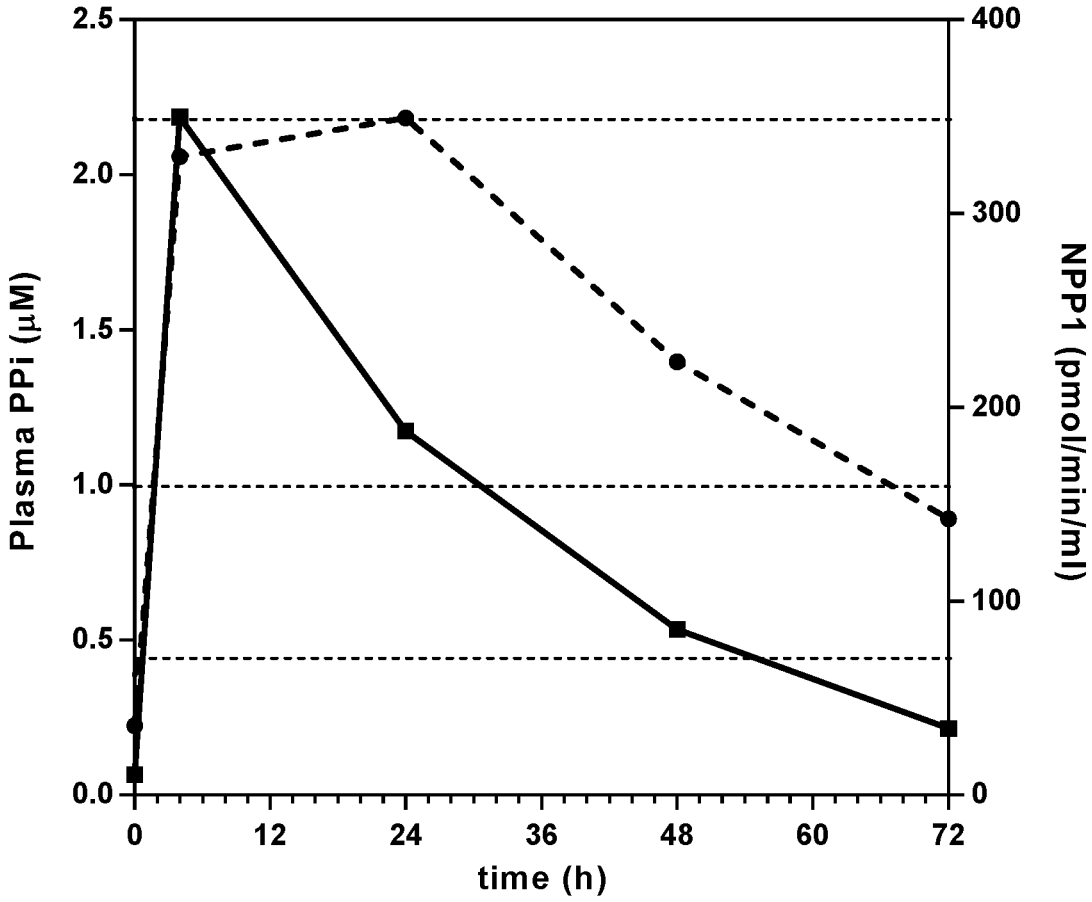
FIG. 7 illustrates blood PPi and enzymatic activity levels in Enpp1(−/−) mice treated with 6 mg/kg sNPP1-Fc-D10 intravenously. Plasma at time points of 0, 4, 24, 48, and 72 hours were collected and analyzed for NPP1 activity (dashed) and PPi levels (solid). The wild-type PPi level was determined to be 2.18 μM (data not shown). The dashed lines from top to bottom show the PPi levels for wild-type, heterozygous Enpp1(+/−), and homozygous Enpp1(−/=) asj mice (Li et. al, 2013). The profiles for sNPP1-Fc were similar to those of sNPP1-Fc-D10.

Enpp1(−/−) knock-out mice was treated with 6 mg/kg sNPP1-Fc-D10 intravenously to determine blood PPi and enzymatic activity levels. As shown in FIG. 7, plasma at time points of 0, 4, 24, 48, and 72 hours were collected and analyzed for NPP1 activity (dashed) and PPi levels (solid). The wild-type PPi level was determined to be 2.18 μM (data not shown). The dashed lines from top to bottom show the PPi levels for wild-type, heterozygous Enpp1(+/−), and homozygous Enpp1(−/−) mice (Li et. al, 2013). The profiles for sNPP1-Fc were similar to those of sNPP1-Fc-D10.

Example IV

Figure 8:
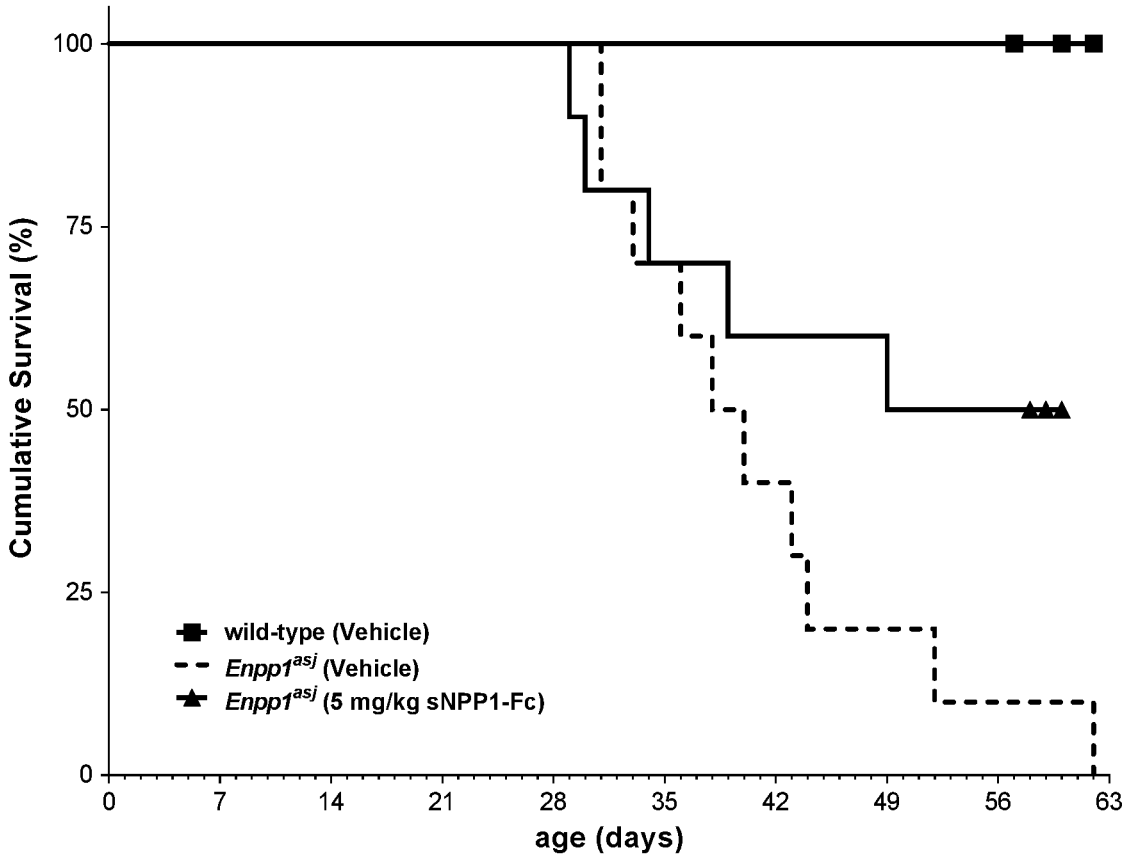
FIG. 8 illustrates increased survival of $Enpp1^{asj}$ homozygous male mice treated with 5 mg/kg sNPP1-Fc in comparison to vehicle treated mice. Wild-type and $Enpp1^{asj}$ mice were placed on a high phosphorus, low magnesium diet starting at birth. Vehicle or sNPP1-Fc (5 mg/kg) was dose subcutaneously every other day starting at 14 days of age. Kaplan-Meier survival curves showed that >50% of asj mice died prior to 6 weeks, and all animals died by 9 weeks. In comparison, 50% of sNPP1-Fc treated animals survived past 7 week and are still living at 9 weeks.

Wild-type and Enpp1$^{asj}$ mice were placed on a high phosphorus, low magnesium diet starting at birth. Vehicle or sNPP1-Fc (5 mg/kg) was dose subcutaneously every other day starting at 14 days of age. Kaplan-Meier survival curves showed that >50% of asj mice died prior to 6 weeks, and all animals died by 9 weeks. In comparison, 50% of sNPP1-Fc treated animals survived past 7 week and are still living at 9 weeks. FIG. 8 illustrates increased survival of Enpp1$^{asj}$ homozygous male mice treated with 5 mg/kg sNPP1-Fc in comparison to vehicle treated mice.

Example V

Figure 9A:
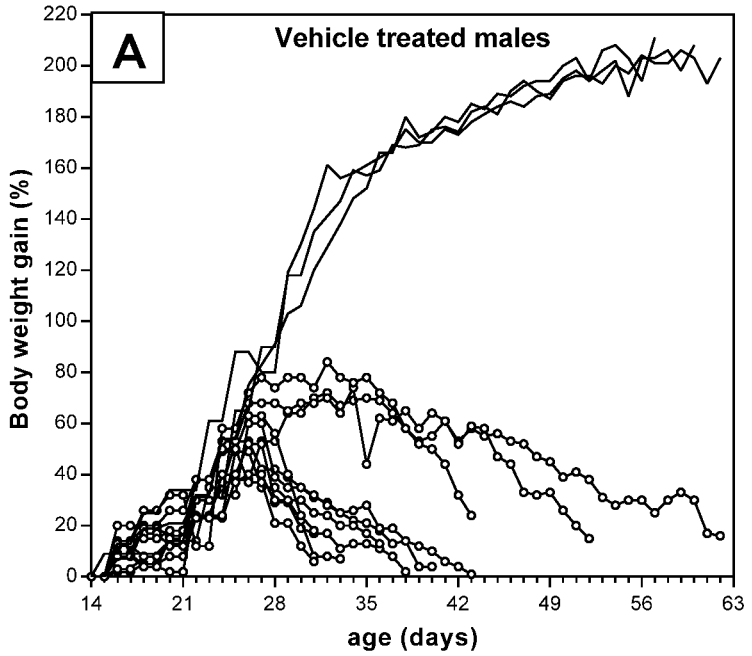
FIGS. 9A and 9B illustrate increased percent body weight gain of $Enpp1^{asj}$ male mice treated with 5 mg/kg sNPP1-Fc (FIG. 9B) in comparison to vehicle treated mice (FIG. 9A). Wild-type and $Enpp1^{asj}$ mice were placed on a high phosphorus, low magnesium diet starting at birth. Vehicle or sNPP1-Fc (5 mg/kg) was injected subcutaneously every other day starting at 14 days of age. Percent body weight gain for wild-type (solid line) and Enpp1$^{asj}$ (circles) mice were plotted from two to nine weeks of age. All Enpp1$^{asj}$ animals were dead (open circle) in the vehicle group at nine weeks (upper panel). In comparison, five Enpp1$^{asj}$ mice were alive (solid circle) and five were dead (open circle) in the sNPP1-Fc treatment group at the end of nine weeks.
Figure 9B:
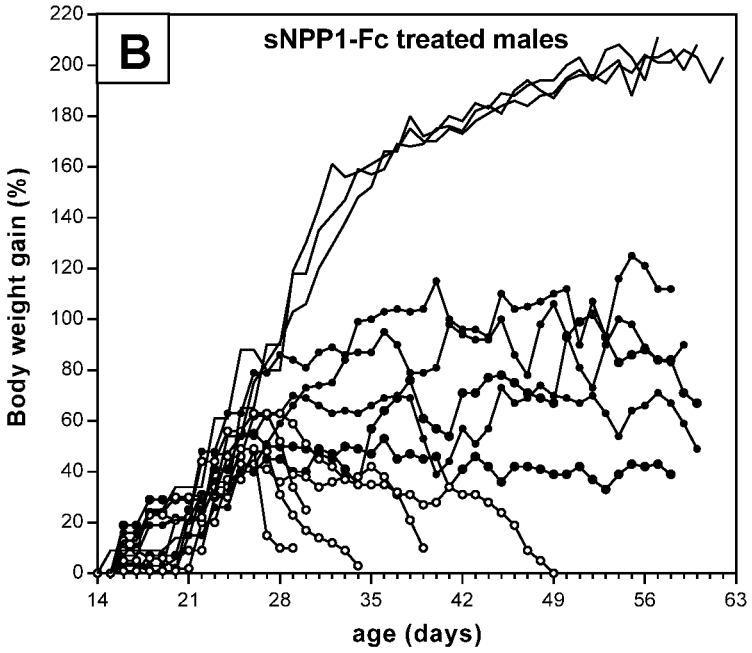
Figures 10A, 10B, 10C:
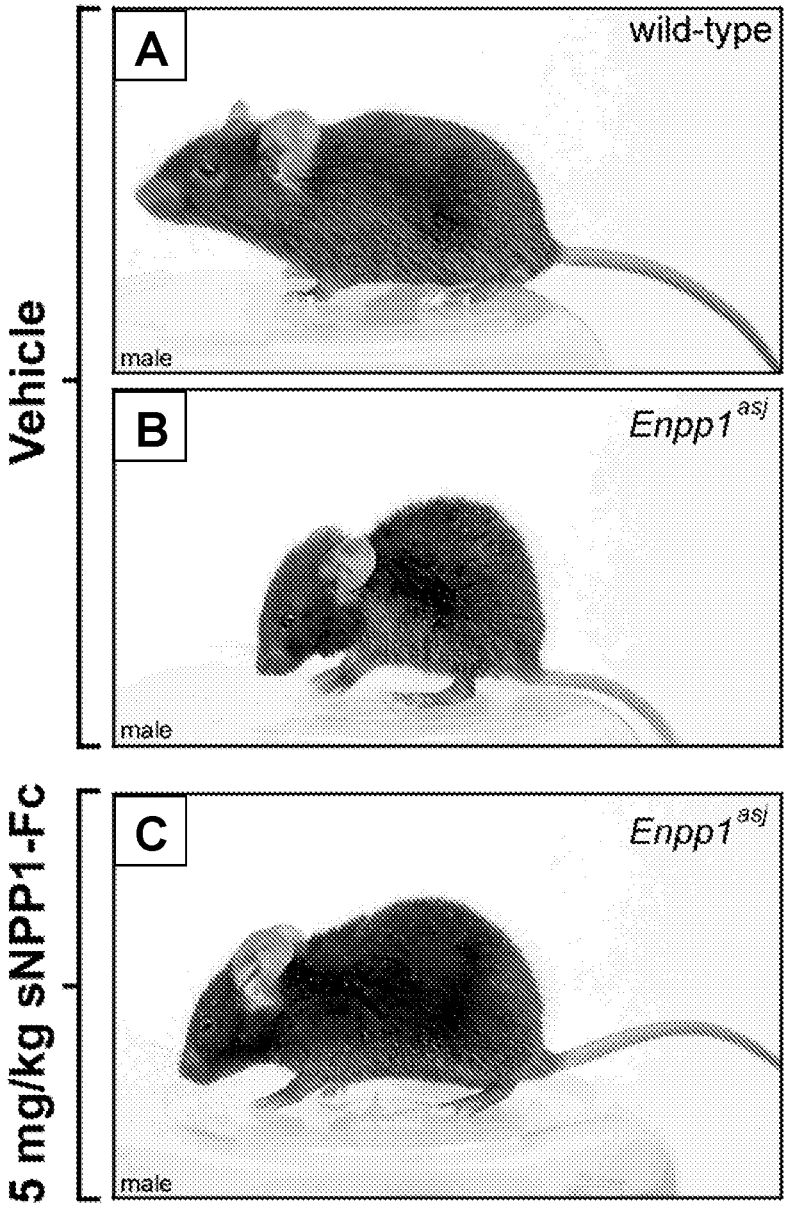
FIGS. 10A-10C are photographs of wild-type (FIG. 10A, top), vehicle treated Enpp1$^{asj}$ (FIG. 10B, middle) sNPP1-Fc treated (5 mg/Kg) treated Enpp1$^{asj}$ (FIG. 10C, bottom) mice.

Wild-type and Enpp1$^{asj}$ mice were placed on a high phosphorus, low magnesium diet starting at birth and treated with vehicle or sNPP1-Fc (5 mg/kg) subcutaneously every other day starting at 14 days of age to determine growth rates. As shown in FIGS. 9A and 9B, percent body weight gain for wild-type (solid line) and Enpp1$^{asj}$ (circles) mice were plotted from two to nine weeks of age. FIGS. 9A and 9B illustrates increased percent body weight gain of Enpp1$^{asj}$ male mice treated with 5 mg/kg sNPP1-Fc in comparison to vehicle treated mice. All Enpp1$^{asj}$ animals were dead (open circle) in the vehicle group at nine weeks (upper panel). In comparison, five Enpp1$^{asj}$ mice were alive (solid circle) and five were dead (open circle) in the sNPP1-Fc treatment group at the end of nine weeks. FIGS. 10A-10C illustrate pictures of wild-type (FIG. 10A, top), vehicle treated Enpp1$^{asj}$ (FIG. 10B, middle) sNPP1-Fc treated (5mg/Kg) treated Enpp1$^{asj}$ (FIG. 10C, bottom) mice.

Example VI

FGF-23 (Fibroblast growth factor 23), a biomarker for phosphate metabolism, was measure in wild-type and Enpp1$^{asj}$ male mice. Wild-type and Enpp1$^{asj}$ mice were placed on a high phosphorus, low magnesium diet (TD.00442, Harlan) starting at birth. Vehicle or sNPP1-Fc-D10 (5 mg/kg) was dosed subcutaneously every other day starting at 18 days of age. All serum was collected 24 hours after dosing and analyzed using a mouse FGF-23 ELISA kit (Kainos Laboratories Inc., Tokyo, Japan). FGF-23 levels were measured at baseline (day 0), prior to initiation of treatment and during the course of treatment in Enpp1$^{+/+}$-Vehicle (solid black), Enpp1$^{asj/asj}$-Vehicle (dotted black), and Enpp1$^{asj/asj}$-sNPP1-Fc-D10 (solid grey) mice.

Figure 11:
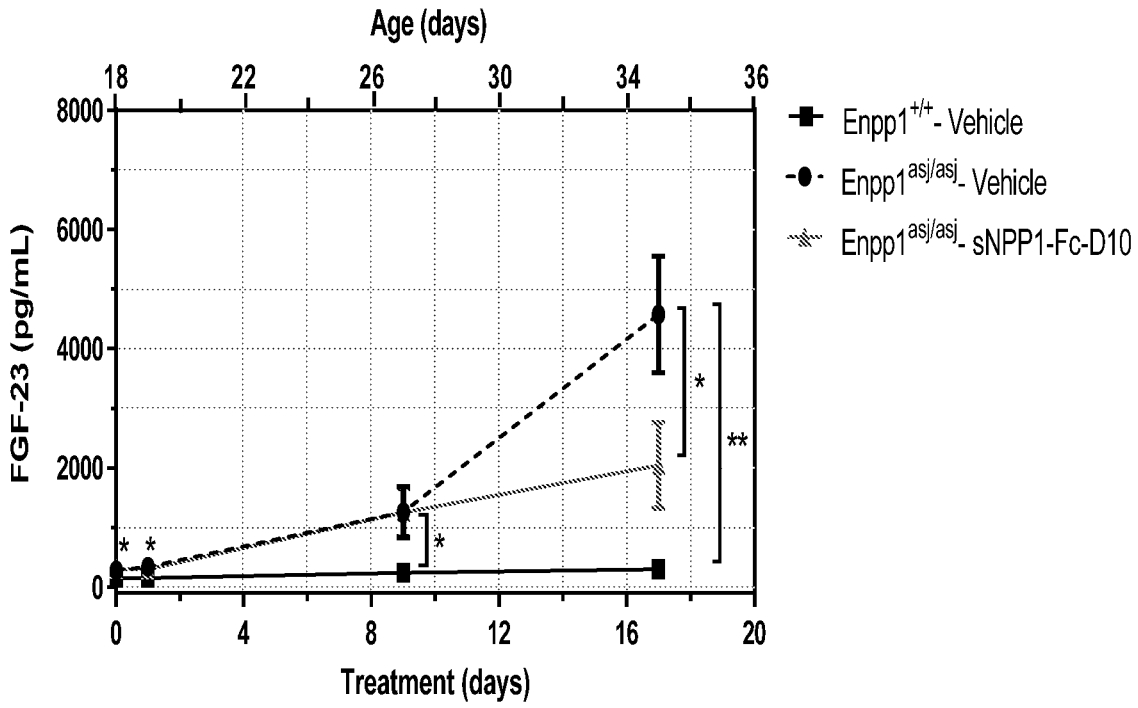
FIG. 11 illustrates levels of fibroblast growth factor 23 in vehicle treated wild-type, vehicle treated Enpp1$^{asj/asj}$, and sNPP1-Fc treated (5 mg/Kg) Enpp1$^{asj/asj}$ mice.

FGF-23 levels were elevated in Enpp1$^{asj/asj}$ mice during the course of disease progression (by day 9 [27 days old]). However, the Enpp1$^{asj/asj}$ mice treated with 5 mg/kg of sNPP1-Fc-D10 showed a decreased level of FGF-23 as compared to the vehicle treated group by day 17 of treatment. *, $p<0.05$ by one-way ANOVA or Student's t-test. FIG. 11 illustrates levels of fibroblast growth factor vehicle treated Enpp1$^{asj/asj}$ (middle) sNPP1-Fc treated (5 mg/Kg) treated Enpp1$^{asj}$ (bottom) mice.

Example VII In Vitro and In Vivo Activity

Figures 13A, 13B, 13C:
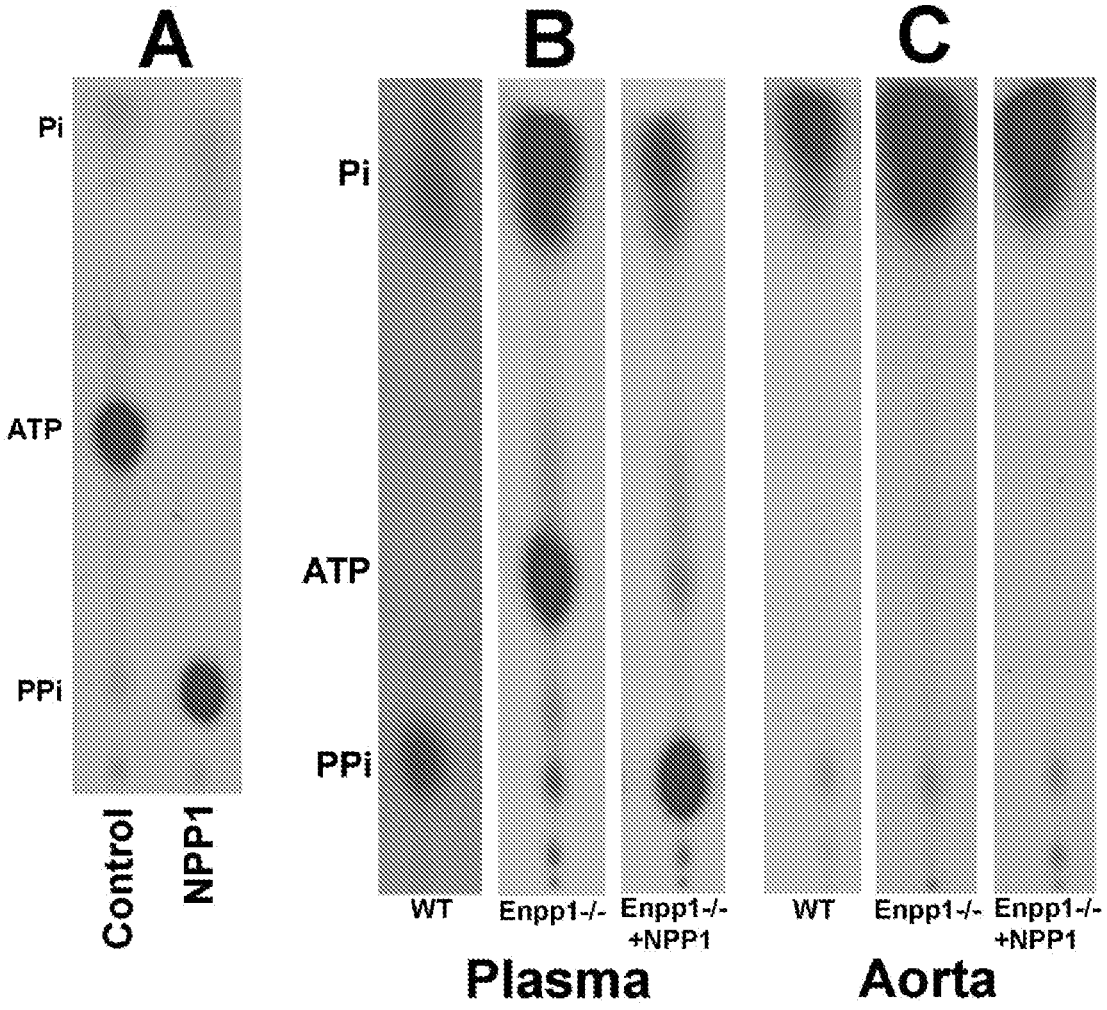
FIGS. 13A-13C are autoradiogram of thin-layer chromatograms which illustrates the activity of recombinant NPP1 in vitro and in vivo.

The recombinant sNPP1-Fc-D10 fully hydrolyzed ATP to PPi in vitro with no hydrolysis of the PPi to orthophosphate as shown in FIG. 13A.

The enzyme activity in plasma is shown in FIG. 13B. Substantial activity was present in the plasma of wild-type mice, with slightly more than one third of the ATP converted to PPi in 10 minutes corresponding to an activity of 7.6±1.0 nmol/h/ml. The remainder was converted to orthophosphate via nucleotide triphosphatases. Plasma from Enpp1$^{-/-}$ mice was essentially devoid of NPP1, with the small amount of PPi representing PPi contaminating the [32P] ATP. Activity was markedly increased to 10.3±0.3 nmol/h/ml two hours after intravenous injection of NPP1 (5 mg/kg) and this was accompanied by an increase in plasma PPi from 0.07±0.02 to 1.00±0.14 uM, compared to a level of 2.39±0.37 uM in wild-type mice.

NPP1 activity was not detectable in aortas from either wild-type or Enpp1$^{-/-}$ mice and did not increase after injection of NPP1 as shown in FIG. 13C. Activity was also not detected in liver after the administration of recombinant NPP1.

Figures 14A, 14B:
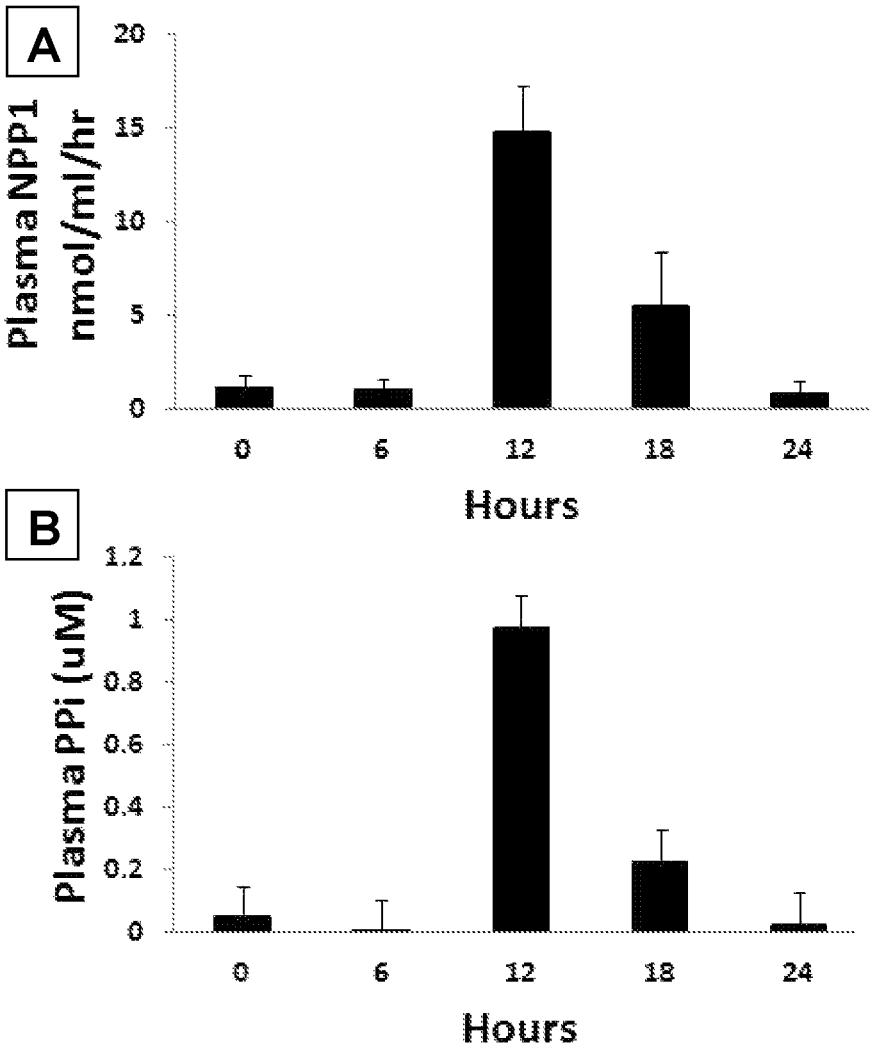
FIGS. 14A and 14B are histograms which illustrates the time course of plasma NPP1 activity (FIG. 14A, top) and plasma pyrophosphate concentration (FIG. 14B, bottom) in Enpp1(−/−) mice after subcutaneous injection of recombinant NPP1 (5 mg/kg).

The time course of plasma NPP1 activity and PPi concentration after subcutaneous injection of 5 mg/kg into Enpp1$^{-/-}$ mice is shown in FIG. 14. NPP1 activity and PPi concentration peaked 12 hours after injection at levels that were 195% and 41% respectively of those in wild-type littermates. The levels decreased rapidly and were essentially undetectable after 24 hours.

Figure 15:
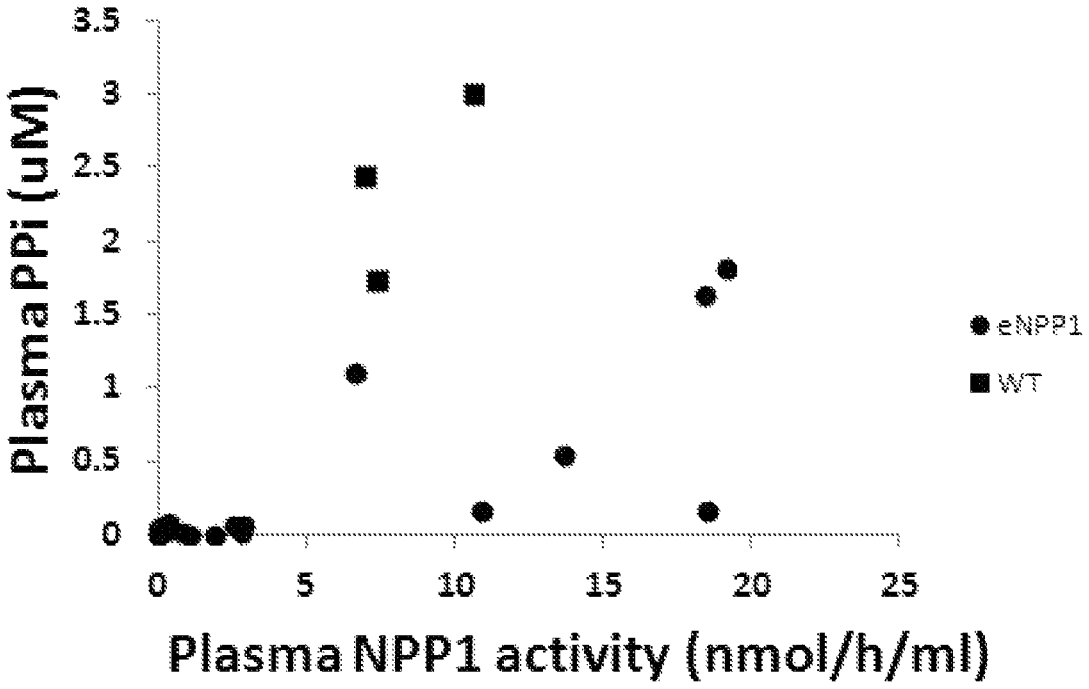
FIG. 15 is a scatter-plot which illustrates the relationship between plasma NPP1 activity and plasma pyrophosphate (PPi) for Enpp1(−/−) mice at various times after subcutaneous injection of recombinant NPP1 (5 mg/kg) (circles) and for wild-type mice (squares).

Subcutaneous injection of sNPP1-Fc-D10 (5 mg/kg) shows a correlation between the plasma PPi levels and plasma NPP1 activity as shown in FIG. 15. The correlation of plasma PPi with plasma NPP1 suggested that the PPi was generated in the circulation. This was examined by incubating fresh human blood with recombinant NPP1 and then measuring PPi in the plasma. Human blood was used because of the limited amount of blood obtainable from mice. The amount of NPP1 added to the blood was calculated so as to yield levels similar to those achieved after injection in mice.

Figures 16A, 16B, 16C:
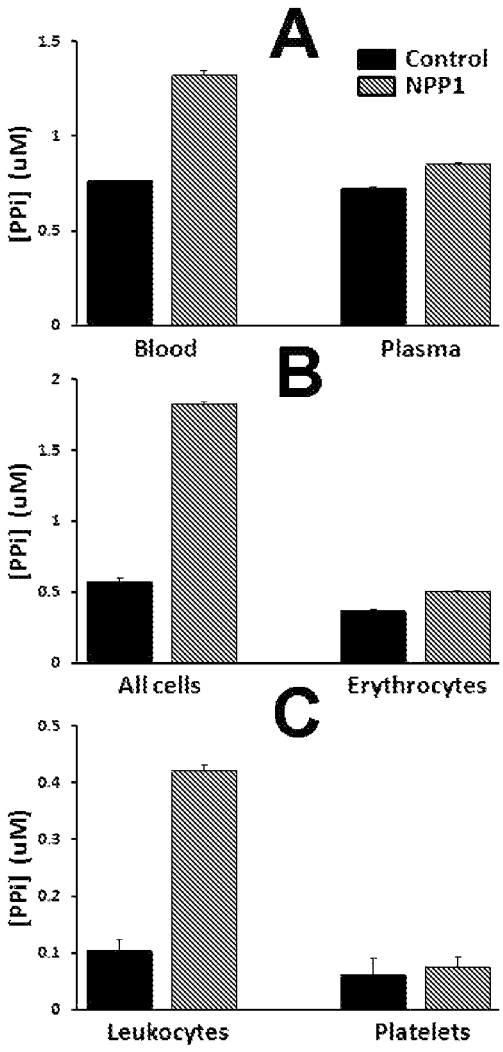
FIGS. 16A-16C are histograms which illustrates the synthesis of pyrophosphate in human blood.

FIG. 16A illustrates that administration of recombinant NPP1 increased plasma PPi when added to whole blood for 2 hours but not when added to plasma alone, indicating a cellular requirement. To examine the role of erythrocytes versus other cells, blood was centrifuged and plasma was removed either with or without the buffy coat remaining. HEPES-buffered saline was then added to restore the original hematocrit. As shown in FIG. 16B, production only occurred when the buffy coat was retained, indicating a requirement for leukocytes or platelets but not erythrocytes. Incubation of isolated leukocytes or platelets in HEPES-buffered saline indicated that both either released or produced PPi but that synthesis in response to exogenous NPP1 occurred only with leukocytes as shown in FIG. 16C.

Example VIII Therapeutic Models

A. NPP1 Deficiency

Figure 17:
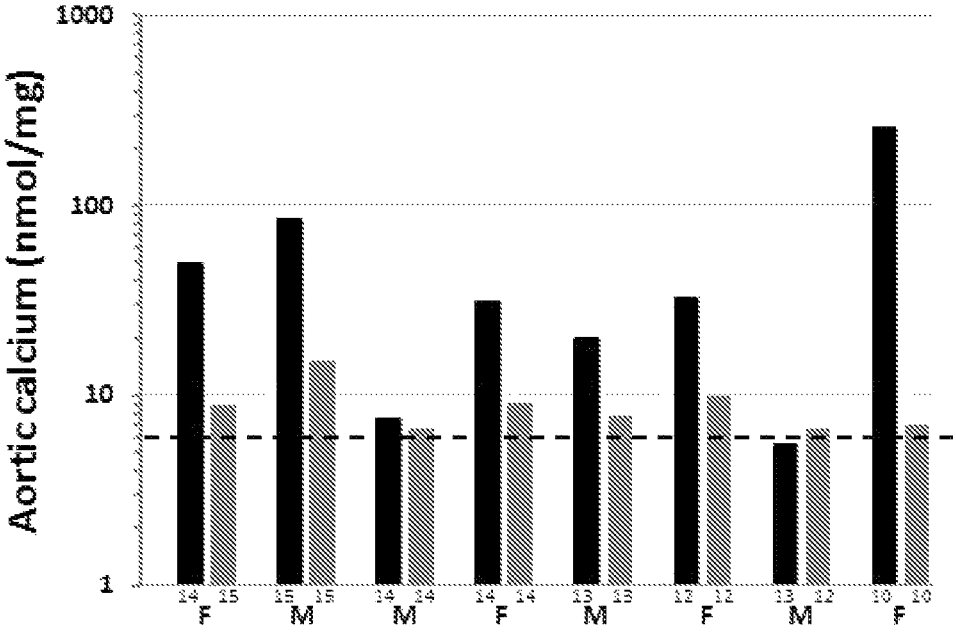
FIG. 17 is a histogram which illustrates the effect of recombinant NPP1 on aortic calcification in Enpp1(−/−) mice. Recombinant NPP1 was injected (6 mg/kg) subcutaneously every 48 hours in mice fed with a high phosphate diet. Each bar represents a single animal with age in weeks given underneath. M: male pair; F: female pair. Dashed line indicates the mean calcium content of aortas from wild-type littermates.

Enpp1$^{-/-}$ mice aged were placed on a high phosphate diet and treated with vehicle or sNPP1-Fc-D10 (6 mg/kg) subcutaneously every other day as shown in FIG. 17 to determine the effect of recombinant NPP1 on arterial calcification. Each treated mouse was paired with a mouse of the same gender and similar age that received the same volume of vehicle alone. After 18 days, the mean aortic calcium content was 61±30 nmol/mg in the vehicle-treated mice and 8.8±1.0 nmol/mg in the mice treated with recombinant NPP1 (p=0.016). The content in wild-type littermates was 6.3±3.4 nmol/mg (n=16). Content was elevated (two standard deviations above wild-type littermates) in 6 of 8 control aortas (80±37 nmol/mg) and in only one treated aorta (15 nmol/mg). Within the pairs in which calcification was present in control aortas, this represented a 91±2% decrease in calcification.

To determine whether there is any accumulation of NPP1 after multiple injections over time, plasma NPP1 activity and PPi, measured at sacrifice (24 hours after injection), and were both undetectable. In a separate set of Enpp1$^{-/-}$ mice, aortic NPP1 activity was undetectable after 3 injections of recombinant NPP1 every other day.

B. Chronic Kidney Disease

Figure 18:
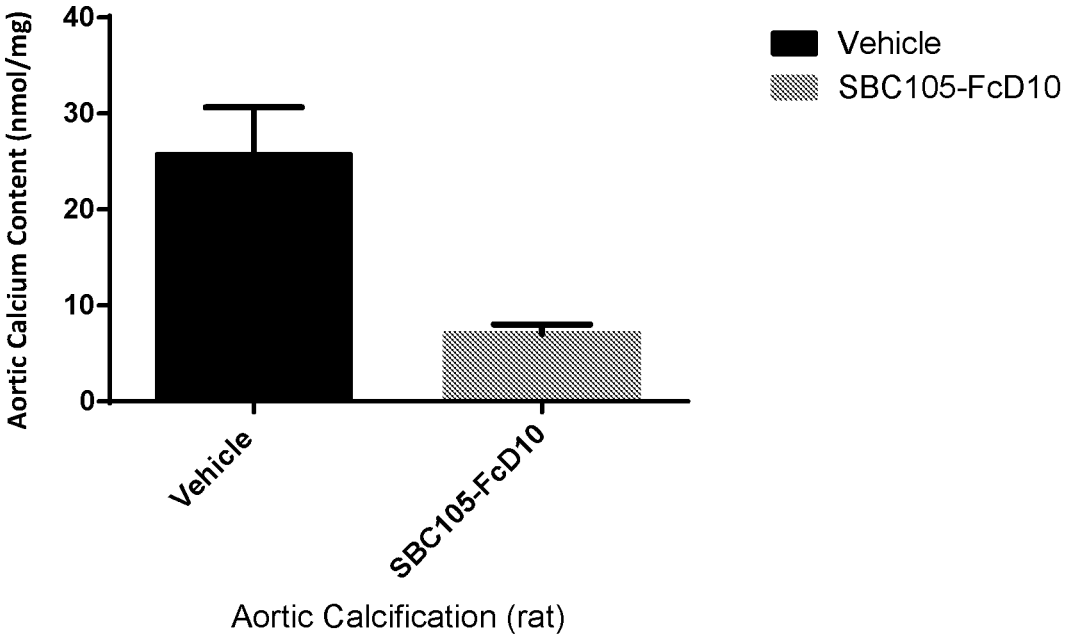
FIG. 18 is a histogram which illustrates the effect of recombinant NPP1 on aortic calcification in uremic rats with renal failure. sNPP1-Fc-D10 or control was injected (5 mg/kg) subcutaneously, 5 dose per week for 21 days in uremic rats fed with a high adenine diet. Each bar represents a single animal aged approximately 4 months.

This example discloses the efficacy of sNPP1-Fc-D10 in treating chronic kidney disease (CKD) in uremic rat models. To determine the effect of recombinant NPP1 on arterial calcification in uremic rats with renal failure, the uremic rats were fed a high adenine diet and injected subcutaneously with control or sNPP1-Fc-D10 (5 mg/kg), 5 dose per week as illustrated in FIG. 18. After 21 days of treatment, the mean aortic calcium content was 25.7±4.9 nmol/mg in the control-treated rat and 7.0±1.0 nmol/mg in the rat treated with recombinant NPP1 (p=0.0068). The normal aortic calcium content was 5 nmol/mg.

Examples VII and VIII demonstrate the activity of sNPP1 and effective use of sNPP1 in models of ectonucleotide pyrophosphate pyrophosphorylase deficiency and chronic kidney disease. These examples show that a transient increase in PPi is sufficient for an effective therapy of vascular calcification and NPP1 deficiency.

EQUIVALENTS

While this invention has been particularly shown and described with references to example embodiments thereof, it will be understood by those skilled in the art that various changes in form and details may be made therein without departing from the scope of the invention encompassed by the appended claims.

---

SEQUENCE LISTING

```
<160> NUMBER OF SEQ ID NOS: 19

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
```

```
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445
```

```
Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
    850                 855                 860
```

```
Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
        915                 920                 925


<210> SEQ ID NO 2
<211> LENGTH: 827
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30

Asn Cys Cys Leu Asp Tyr Gln Glu Thr Cys Ile Glu Pro Glu His Ile
        35                  40                  45

Trp Thr Cys Asn Lys Phe Arg Cys Gly Glu Lys Arg Leu Thr Arg Ser
    50                  55                  60

Leu Cys Ala Cys Ser Asp Asp Cys Lys Asp Lys Gly Asp Cys Cys Ile
65                  70                  75                  80

Asn Tyr Ser Ser Val Cys Gln Gly Glu Lys Ser Trp Val Glu Glu Pro
                85                  90                  95

Cys Glu Ser Ile Asn Glu Pro Gln Cys Pro Ala Gly Phe Glu Thr Pro
            100                 105                 110

Pro Thr Leu Leu Phe Ser Leu Asp Gly Phe Arg Ala Glu Tyr Leu His
        115                 120                 125

Thr Trp Gly Gly Leu Leu Pro Val Ile Ser Lys Leu Lys Lys Cys Gly
    130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
        195                 200                 205

Trp Val Thr Ala Lys Tyr Gln Gly Leu Lys Ser Gly Thr Phe Phe Trp
    210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                245                 250                 255

Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
        275                 280                 285

Ser Glu Val Ile Lys Ala Leu Gln Arg Val Asp Gly Met Val Gly Met
    290                 295                 300
```

```
Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                325                 330                 335

Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
        355                 360                 365

Tyr Ser Phe Asn Tyr Glu Gly Ile Ala Arg Asn Leu Ser Cys Arg Glu
    370                 375                 380

Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
        435                 440                 445

Leu Phe Val Gly Tyr Gly Pro Gly Phe Lys His Gly Ile Glu Ala Asp
    450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
        515                 520                 525

Ser Cys Asn Pro Ser Ile Leu Pro Ile Glu Asp Phe Gln Thr Gln Phe
    530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
        595                 600                 605

Asp Phe Ser Asn Cys Leu Tyr Gln Asp Phe Arg Ile Pro Leu Ser Pro
    610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
            660                 665                 670

Val Ile Trp Arg Tyr Phe His Asp Thr Leu Leu Arg Lys Tyr Ala Glu
        675                 680                 685

Glu Arg Asn Gly Val Asn Val Val Ser Gly Pro Val Phe Asp Phe Asp
    690                 695                 700

Tyr Asp Gly Arg Cys Asp Ser Leu Glu Asn Leu Arg Gln Lys Arg Arg
705                 710                 715                 720
```

```
Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
        755                 760                 765

Ser Cys Val His Gly Lys His Asp Ser Ser Trp Val Glu Glu Leu Leu
    770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp
            820                 825


<210> SEQ ID NO 3
<211> LENGTH: 1058
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30

Asn Cys Cys Leu Asp Tyr Gln Glu Thr Cys Ile Glu Pro Glu His Ile
        35                  40                  45

Trp Thr Cys Asn Lys Phe Arg Cys Gly Glu Lys Arg Leu Thr Arg Ser
    50                  55                  60

Leu Cys Ala Cys Ser Asp Asp Cys Lys Asp Lys Gly Asp Cys Cys Ile
65                  70                  75                  80

Asn Tyr Ser Ser Val Cys Gln Gly Glu Lys Ser Trp Val Glu Glu Pro
                85                  90                  95

Cys Glu Ser Ile Asn Glu Pro Gln Cys Pro Ala Gly Phe Glu Thr Pro
            100                 105                 110

Pro Thr Leu Leu Phe Ser Leu Asp Gly Phe Arg Ala Glu Tyr Leu His
        115                 120                 125

Thr Trp Gly Gly Leu Leu Pro Val Ile Ser Lys Leu Lys Lys Cys Gly
    130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
        195                 200                 205

Trp Val Thr Ala Lys Tyr Gln Gly Leu Lys Ser Gly Thr Phe Phe Trp
    210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                245                 250                 255
```

```
Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
        275                 280                 285

Ser Glu Val Ile Lys Ala Leu Gln Arg Val Asp Gly Met Val Gly Met
    290                 295                 300

Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                325                 330                 335

Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
        355                 360                 365

Tyr Ser Phe Asn Tyr Glu Gly Ile Ala Arg Asn Leu Ser Cys Arg Glu
    370                 375                 380

Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
        435                 440                 445

Leu Phe Val Gly Tyr Gly Pro Gly Phe Lys His Gly Ile Glu Ala Asp
    450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
        515                 520                 525

Ser Cys Asn Pro Ser Ile Leu Pro Ile Glu Asp Phe Gln Thr Gln Phe
    530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
        595                 600                 605

Asp Phe Ser Asn Cys Leu Tyr Gln Asp Phe Arg Ile Pro Leu Ser Pro
    610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
            660                 665                 670
```

```
Val Ile Trp Arg Tyr Phe His Asp Thr Leu Leu Arg Lys Tyr Ala Glu
        675                 680                 685

Glu Arg Asn Gly Val Asn Val Val Ser Gly Pro Val Phe Asp Phe Asp
    690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
        755                 760                 765

Ser Cys Val His Gly Lys His Asp Ser Ser Trp Val Glu Glu Leu Leu
    770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp Pro Lys Ser Cys Asp
            820                 825                 830

Lys Thr His Thr Cys Pro Pro Cys Pro Ala Pro Glu Ala Ala Gly Ala
        835                 840                 845

Pro Ser Val Phe Leu Phe Pro Pro Lys Pro Lys Asp Thr Leu Met Ile
    850                 855                 860

Ser Arg Thr Pro Glu Val Thr Cys Val Val Val Asp Val Ser His Glu
865                 870                 875                 880

Asp Pro Glu Val Lys Phe Asn Trp Tyr Val Asp Gly Val Glu Val His
                885                 890                 895

Asn Ala Lys Thr Lys Pro Arg Glu Glu Gln Tyr Asn Ser Thr Tyr Arg
            900                 905                 910

Val Val Ser Val Leu Thr Val Leu His Gln Asp Trp Leu Asn Gly Lys
        915                 920                 925

Glu Tyr Lys Cys Lys Val Ser Asn Lys Ala Leu Pro Ala Pro Ile Glu
    930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
                965                 970                 975

Thr Cys Leu Val Lys Gly Phe Tyr Pro Ser Asp Ile Ala Val Glu Trp
            980                 985                 990

Glu Ser Asn Gly Gln Pro Glu Asn  Asn Tyr Lys Thr Thr  Pro Pro Val
        995                 1000                1005

Leu Asp  Ser Asp Gly Ser Phe  Phe Leu Tyr Ser Lys  Leu Thr Val
    1010                1015                1020

Asp Lys  Ser Arg Trp Gln Gln  Gly Asn Val Phe Ser  Cys Ser Val
    1025                1030                1035

Met His  Glu Ala Leu His Asn  His Tyr Thr Gln Lys  Ser Leu Ser
    1040                1045                1050

Leu Ser  Pro Gly Lys
    1055


<210> SEQ ID NO 4
<211> LENGTH: 1068
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 4

Pro Ser Cys Ala Lys Glu Val Lys Ser Cys Lys Gly Arg Cys Phe Glu
1 5 10 15

Arg Thr Phe Gly Asn Cys Arg Cys Asp Ala Ala Cys Val Glu Leu Gly
20 25 30

Asn Cys Cys Leu Asp Tyr Gln Glu Thr Cys Ile Glu Pro Glu His Ile
35 40 45

Trp Thr Cys Asn Lys Phe Arg Cys Gly Glu Lys Arg Leu Thr Arg Ser
50 55 60

Leu Cys Ala Cys Ser Asp Asp Cys Lys Asp Lys Gly Asp Cys Cys Ile
65 70 75 80

Asn Tyr Ser Ser Val Cys Gln Gly Glu Lys Ser Trp Val Glu Glu Pro
85 90 95

Cys Glu Ser Ile Asn Glu Pro Gln Cys Pro Ala Gly Phe Glu Thr Pro
100 105 110

Pro Thr Leu Leu Phe Ser Leu Asp Gly Phe Arg Ala Glu Tyr Leu His
115 120 125

Thr Trp Gly Gly Leu Leu Pro Val Ile Ser Lys Leu Lys Lys Cys Gly
130 135 140

Thr Tyr Thr Lys Asn Met Arg Pro Val Tyr Pro Thr Lys Thr Phe Pro
145 150 155 160

Asn His Tyr Ser Ile Val Thr Gly Leu Tyr Pro Glu Ser His Gly Ile
165 170 175

Ile Asp Asn Lys Met Tyr Asp Pro Lys Met Asn Ala Ser Phe Ser Leu
180 185 190

Lys Ser Lys Glu Lys Phe Asn Pro Glu Trp Tyr Lys Gly Glu Pro Ile
195 200 205

Trp Val Thr Ala Lys Tyr Gln Gly Leu Lys Ser Gly Thr Phe Phe Trp
210 215 220

Pro Gly Ser Asp Val Glu Ile Asn Gly Ile Phe Pro Asp Ile Tyr Lys
225 230 235 240

Met Tyr Asn Gly Ser Val Pro Phe Glu Glu Arg Ile Leu Ala Val Leu
245 250 255

Gln Trp Leu Gln Leu Pro Lys Asp Glu Arg Pro His Phe Tyr Thr Leu
260 265 270

Tyr Leu Glu Glu Pro Asp Ser Ser Gly His Ser Tyr Gly Pro Val Ser
275 280 285

Ser Glu Val Ile Lys Ala Leu Gln Arg Val Asp Gly Met Val Gly Met
290 295 300

Leu Met Asp Gly Leu Lys Glu Leu Asn Leu His Arg Cys Leu Asn Leu
305 310 315 320

Ile Leu Ile Ser Asp His Gly Met Glu Gln Gly Ser Cys Lys Lys Tyr
325 330 335

Ile Tyr Leu Asn Lys Tyr Leu Gly Asp Val Lys Asn Ile Lys Val Ile
340 345 350

Tyr Gly Pro Ala Ala Arg Leu Arg Pro Ser Asp Val Pro Asp Lys Tyr
355 360 365

Tyr Ser Phe Asn Tyr Glu Gly Ile Ala Arg Asn Leu Ser Cys Arg Glu
370 375 380

```
Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
        435                 440                 445

Leu Phe Val Gly Tyr Gly Pro Gly Phe Lys His Gly Ile Glu Ala Asp
    450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
        515                 520                 525

Ser Cys Asn Pro Ser Ile Leu Pro Ile Glu Asp Phe Gln Thr Gln Phe
    530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
        595                 600                 605

Asp Phe Ser Asn Cys Leu Tyr Gln Asp Phe Arg Ile Pro Leu Ser Pro
    610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
            660                 665                 670

Val Ile Trp Arg Tyr Phe His Asp Thr Leu Leu Arg Lys Tyr Ala Glu
        675                 680                 685

Glu Arg Asn Gly Val Asn Val Val Ser Gly Pro Val Phe Asp Phe Asp
    690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
        755                 760                 765

Ser Cys Val His Gly Lys His Asp Ser Ser Trp Val Glu Glu Leu Leu
    770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
```

```
                805                 810                 815

Lys Thr His Leu Pro Thr Phe Ser Gln Glu Asp Pro Lys Ser Cys Asp
            820                 825                 830

Lys Thr His Thr Cys Pro Pro Cys Pro Ala Pro Glu Ala Ala Gly Ala
        835                 840                 845

Pro Ser Val Phe Leu Phe Pro Pro Lys Pro Lys Asp Thr Leu Met Ile
    850                 855                 860

Ser Arg Thr Pro Glu Val Thr Cys Val Val Val Asp Val Ser His Glu
865                 870                 875                 880

Asp Pro Glu Val Lys Phe Asn Trp Tyr Val Asp Gly Val Glu Val His
                885                 890                 895

Asn Ala Lys Thr Lys Pro Arg Glu Glu Gln Tyr Asn Ser Thr Tyr Arg
            900                 905                 910

Val Val Ser Val Leu Thr Val Leu His Gln Asp Trp Leu Asn Gly Lys
        915                 920                 925

Glu Tyr Lys Cys Lys Val Ser Asn Lys Ala Leu Pro Ala Pro Ile Glu
    930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
                965                 970                 975

Thr Cys Leu Val Lys Gly Phe Tyr Pro Ser Asp Ile Ala Val Glu Trp
            980                 985                 990

Glu Ser Asn Gly Gln Pro Glu Asn  Asn Tyr Lys Thr Thr  Pro Pro Val
        995                 1000                1005

Leu Asp  Ser Asp Gly Ser Phe  Phe Leu Tyr Ser Lys  Leu Thr Val
    1010                1015                1020

Asp Lys  Ser Arg Trp Gln Gln  Gly Asn Val Phe Ser  Cys Ser Val
    1025                1030                1035

Met His  Glu Ala Leu His Asn  His Tyr Thr Gln Lys  Ser Leu Ser
    1040                1045                1050

Leu Ser  Pro Gly Lys Asp Asp  Asp Asp Asp Asp Asp  Asp Asp Asp
    1055                1060                1065


<210> SEQ ID NO 5
<211> LENGTH: 819
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95
```

```
Cys Pro Ala Gly Phe Glu Thr Pro Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
    130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
    370                 375                 380

Leu Lys His Phe Leu Pro Lys Arg Leu His Phe Ala Lys Ser Asp Arg
385                 390                 395                 400

Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
    450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
                485                 490                 495

Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
```

```
        515                 520                 525

Ile Glu Asp Phe Gln Thr Gln Phe Asn Leu Thr Val Ala Glu Glu Lys
    530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
            580                 585                 590

Arg Asn Asp Ser Phe Ser Thr Glu Asp Phe Ser Asn Cys Leu Tyr Gln
        595                 600                 605

Asp Phe Arg Ile Pro Leu Ser Pro Val His Lys Cys Ser Phe Tyr Lys
    610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
        675                 680                 685

Ser Gly Pro Val Phe Asp Phe Asp Tyr Asp Gly Arg Cys Asp Ser Leu
    690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
        755                 760                 765

Ser Ser Trp Val Glu Glu Leu Leu Met Leu His Arg Ala Arg Ile Thr
    770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp


<210> SEQ ID NO 6
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Lys Ser Trp Val Glu Glu Pro Cys Glu Ser Ile Asn Glu Pro Gln
1               5                   10                  15

Cys Pro Ala Gly Phe Glu Thr Pro Pro Thr Leu Leu Phe Ser Leu Asp
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
```

```
    50                  55                  60

Val Tyr Pro Thr Lys Thr Phe Pro Asn His Tyr Ser Ile Val Thr Gly
65                  70                  75                  80

Leu Tyr Pro Glu Ser His Gly Ile Ile Asp Asn Lys Met Tyr Asp Pro
                85                  90                  95

Lys Met Asn Ala Ser Phe Ser Leu Lys Ser Lys Glu Lys Phe Asn Pro
            100                 105                 110

Glu Trp Tyr Lys Gly Glu Pro Ile Trp Val Thr Ala Lys Tyr Gln Gly
        115                 120                 125

Leu Lys Ser Gly Thr Phe Phe Trp Pro Gly Ser Asp Val Glu Ile Asn
    130                 135                 140

Gly Ile Phe Pro Asp Ile Tyr Lys Met Tyr Asn Gly Ser Val Pro Phe
145                 150                 155                 160

Glu Glu Arg Ile Leu Ala Val Leu Gln Trp Leu Gln Leu Pro Lys Asp
                165                 170                 175

Glu Arg Pro His Phe Tyr Thr Leu Tyr Leu Glu Glu Pro Asp Ser Ser
            180                 185                 190

Gly His Ser Tyr Gly Pro Val Ser Ser Glu Val Ile Lys Ala Leu Gln
        195                 200                 205

Arg Val Asp Gly Met Val Gly Met Leu Met Asp Gly Leu Lys Glu Leu
    210                 215                 220

Asn Leu His Arg Cys Leu Asn Leu Ile Leu Ile Ser Asp His Gly Met
225                 230                 235                 240

Glu Gln Gly Ser Cys Lys Lys Tyr Ile Tyr Leu Asn Lys Tyr Leu Gly
                245                 250                 255

Asp Val Lys Asn Ile Lys Val Ile Tyr Gly Pro Ala Ala Arg Leu Arg
            260                 265                 270

Pro Ser Asp Val Pro Asp Lys Tyr Tyr Ser Phe Asn Tyr Glu Gly Ile
        275                 280                 285

Ala Arg Asn Leu Ser Cys Arg Glu Pro Asn Gln His Phe Lys Pro Tyr
    290                 295                 300

Leu Lys His Phe Leu Pro Lys Arg Leu His Phe Ala Lys Ser Asp Arg
305                 310                 315                 320

Ile Glu Pro Leu Thr Phe Tyr Leu Asp Pro Gln Trp Gln Leu Ala Leu
                325                 330                 335

Asn Pro Ser Glu Arg Lys Tyr Cys Gly Ser Gly Phe His Gly Ser Asp
            340                 345                 350

Asn Val Phe Ser Asn Met Gln Ala Leu Phe Val Gly Tyr Gly Pro Gly
        355                 360                 365

Phe Lys His Gly Ile Glu Ala Asp Thr Phe Glu Asn Ile Glu Val Tyr
    370                 375                 380

Asn Leu Met Cys Asp Leu Leu Asn Leu Thr Pro Ala Pro Asn Asn Gly
385                 390                 395                 400

Thr His Gly Ser Leu Asn His Leu Leu Lys Asn Pro Val Tyr Thr Pro
                405                 410                 415

Lys His Pro Lys Glu Val His Pro Leu Val Gln Cys Pro Phe Thr Arg
            420                 425                 430

Asn Pro Arg Asp Asn Leu Gly Cys Ser Cys Asn Pro Ser Ile Leu Pro
        435                 440                 445

Ile Glu Asp Phe Gln Thr Gln Phe Asn Leu Thr Val Ala Glu Glu Lys
    450                 455                 460

Ile Ile Lys His Glu Thr Leu Pro Tyr Gly Arg Pro Arg Val Leu Gln
465                 470                 475                 480
```

```
Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
            500                 505                 510

Arg Asn Asp Ser Phe Ser Thr Glu Asp Phe Ser Asn Cys Leu Tyr Gln
        515                 520                 525

Asp Phe Arg Ile Pro Leu Ser Pro Val His Lys Cys Ser Phe Tyr Lys
    530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
            580                 585                 590

Thr Leu Leu Arg Lys Tyr Ala Glu Glu Arg Asn Gly Val Asn Val Val
        595                 600                 605

Ser Gly Pro Val Phe Asp Phe Asp Tyr Asp Gly Arg Cys Asp Ser Leu
    610                 615                 620

Glu Asn Leu Arg Gln Lys Arg Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Glu Leu Leu Met Leu His Arg Ala Arg Ile Thr
    690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp


<210> SEQ ID NO 7
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 8
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

```
    210                 215                 220

Pro Gly Lys
225


<210> SEQ ID NO 9
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
    130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335
```

```
Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
    370                 375                 380

Leu Lys His Phe Leu Pro Lys Arg Leu His Phe Ala Lys Ser Asp Arg
385                 390                 395                 400

Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
    450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
                485                 490                 495

Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
        515                 520                 525

Ile Glu Asp Phe Gln Thr Gln Phe Asn Leu Thr Val Ala Glu Glu Lys
    530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
            580                 585                 590

Arg Asn Asp Ser Phe Ser Thr Glu Asp Phe Ser Asn Cys Leu Tyr Gln
        595                 600                 605

Asp Phe Arg Ile Pro Leu Ser Pro Val His Lys Cys Ser Phe Tyr Lys
    610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
        675                 680                 685

Ser Gly Pro Val Phe Asp Phe Asp Tyr Asp Gly Arg Cys Asp Ser Leu
    690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
```

```
        755                 760                 765

Ser Ser Trp Val Glu Glu Leu Leu Met Leu His Arg Ala Arg Ile Thr
    770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp Glu Pro Lys Ser Cys Asp Lys Thr His Thr Cys Pro Pro
            820                 825                 830

Cys Pro Ala Pro Glu Leu Leu Gly Gly Pro Ser Val Phe Leu Phe Pro
        835                 840                 845

Pro Lys Pro Lys Asp Thr Leu Met Ile Ser Arg Thr Pro Glu Val Thr
    850                 855                 860

Cys Val Val Val Asp Val Ser His Glu Asp Pro Glu Val Lys Phe Asn
865                 870                 875                 880

Trp Tyr Val Asp Gly Val Glu Val His Asn Ala Lys Thr Lys Pro Arg
                885                 890                 895

Glu Glu Gln Tyr Asn Ser Thr Tyr Arg Val Val Ser Val Leu Thr Val
            900                 905                 910

Leu His Gln Asp Trp Leu Asn Gly Lys Glu Tyr Lys Cys Lys Val Ser
        915                 920                 925

Asn Lys Ala Leu Pro Ala Pro Ile Glu Lys Thr Ile Ser Lys Ala Lys
    930                 935                 940

Gly Gln Pro Arg Glu Pro Gln Val Tyr Thr Leu Pro Pro Ser Arg Glu
945                 950                 955                 960

Glu Met Thr Lys Asn Gln Val Ser Leu Thr Cys Leu Val Lys Gly Phe
                965                 970                 975

Tyr Pro Ser Asp Ile Ala Val Glu Trp Glu Ser Asn Gly Gln Pro Glu
            980                 985                 990

Asn Asn Tyr Lys Thr Thr Pro Pro  Val Leu Asp Ser Asp  Gly Ser Phe
        995                 1000                1005

Phe Leu  Tyr Ser Lys Leu Thr  Val Asp Lys Ser Arg  Trp Gln Gln
    1010                1015                1020

Gly Asn  Val Phe Ser Cys Ser  Val Met His Glu Ala  Leu His Asn
    1025                1030                1035

His Tyr  Thr Gln Lys Ser Leu  Ser Leu Ser Pro Gly  Lys
    1040                1045                1050


<210> SEQ ID NO 10
<211> LENGTH: 1046
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60
```

```
Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
    130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
    370                 375                 380

Leu Lys His Phe Leu Pro Lys Arg Leu His Phe Ala Lys Ser Asp Arg
385                 390                 395                 400

Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
    450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
```

```
                485                 490                 495

Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
        515                 520                 525

Ile Glu Asp Phe Gln Thr Gln Phe Asn Leu Thr Val Ala Glu Glu Lys
    530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
            580                 585                 590

Arg Asn Asp Ser Phe Ser Thr Glu Asp Phe Ser Asn Cys Leu Tyr Gln
        595                 600                 605

Asp Phe Arg Ile Pro Leu Ser Pro Val His Lys Cys Ser Phe Tyr Lys
    610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
        675                 680                 685

Ser Gly Pro Val Phe Asp Phe Asp Tyr Asp Gly Arg Cys Asp Ser Leu
    690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
        755                 760                 765

Ser Ser Trp Val Glu Glu Leu Leu Met Leu His Arg Ala Arg Ile Thr
    770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp Asp Lys Thr His Thr Cys Pro Pro Cys Pro Ala Pro Glu
            820                 825                 830

Leu Leu Gly Gly Pro Ser Val Phe Leu Phe Pro Pro Lys Pro Lys Asp
        835                 840                 845

Thr Leu Met Ile Ser Arg Thr Pro Glu Val Thr Cys Val Val Val Asp
    850                 855                 860

Val Ser His Glu Asp Pro Glu Val Lys Phe Asn Trp Tyr Val Asp Gly
865                 870                 875                 880

Val Glu Val His Asn Ala Lys Thr Lys Pro Arg Glu Glu Gln Tyr Asn
                885                 890                 895

Ser Thr Tyr Arg Val Val Ser Val Leu Thr Val Leu His Gln Asp Trp
            900                 905                 910
```

```
Leu Asn Gly Lys Glu Tyr Lys Cys Lys Val Ser Asn Lys Ala Leu Pro
        915                 920                 925

Ala Pro Ile Glu Lys Thr Ile Ser Lys Ala Lys Gly Gln Pro Arg Glu
    930                 935                 940

Pro Gln Val Tyr Thr Leu Pro Pro Ser Arg Glu Glu Met Thr Lys Asn
945                 950                 955                 960

Gln Val Ser Leu Thr Cys Leu Val Lys Gly Phe Tyr Pro Ser Asp Ile
                965                 970                 975

Ala Val Glu Trp Glu Ser Asn Gly Gln Pro Glu Asn Asn Tyr Lys Thr
            980                 985                 990

Thr Pro Pro Val Leu Asp Ser Asp  Gly Ser Phe Phe Leu  Tyr Ser Lys
        995                 1000                1005

Leu Thr  Val Asp Lys Ser Arg  Trp Gln Gln Gly Asn  Val Phe Ser
    1010                1015                1020

Cys Ser  Val Met His Glu Ala  Leu His Asn His Tyr  Thr Gln Lys
    1025                1030                1035

Ser Leu  Ser Leu Ser Pro Gly  Lys
    1040                1045


<210> SEQ ID NO 11
<211> LENGTH: 971
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Lys Ser Trp Val Glu Glu Pro Cys Glu Ser Ile Asn Glu Pro Gln
1               5                   10                  15

Cys Pro Ala Gly Phe Glu Thr Pro Pro Thr Leu Leu Phe Ser Leu Asp
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
    50                  55                  60

Val Tyr Pro Thr Lys Thr Phe Pro Asn His Tyr Ser Ile Val Thr Gly
65                  70                  75                  80

Leu Tyr Pro Glu Ser His Gly Ile Ile Asp Asn Lys Met Tyr Asp Pro
                85                  90                  95

Lys Met Asn Ala Ser Phe Ser Leu Lys Ser Lys Glu Lys Phe Asn Pro
            100                 105                 110

Glu Trp Tyr Lys Gly Glu Pro Ile Trp Val Thr Ala Lys Tyr Gln Gly
        115                 120                 125

Leu Lys Ser Gly Thr Phe Phe Trp Pro Gly Ser Asp Val Glu Ile Asn
    130                 135                 140

Gly Ile Phe Pro Asp Ile Tyr Lys Met Tyr Asn Gly Ser Val Pro Phe
145                 150                 155                 160

Glu Glu Arg Ile Leu Ala Val Leu Gln Trp Leu Gln Leu Pro Lys Asp
                165                 170                 175

Glu Arg Pro His Phe Tyr Thr Leu Tyr Leu Glu Glu Pro Asp Ser Ser
            180                 185                 190

Gly His Ser Tyr Gly Pro Val Ser Ser Glu Val Ile Lys Ala Leu Gln
        195                 200                 205

Arg Val Asp Gly Met Val Gly Met Leu Met Asp Gly Leu Lys Glu Leu
```

```
    210                 215                 220

Asn Leu His Arg Cys Leu Asn Leu Ile Leu Ile Ser Asp His Gly Met
225                 230                 235                 240

Glu Gln Gly Ser Cys Lys Lys Tyr Ile Tyr Leu Asn Lys Tyr Leu Gly
                245                 250                 255

Asp Val Lys Asn Ile Lys Val Ile Tyr Gly Pro Ala Ala Arg Leu Arg
            260                 265                 270

Pro Ser Asp Val Pro Asp Lys Tyr Tyr Ser Phe Asn Tyr Glu Gly Ile
        275                 280                 285

Ala Arg Asn Leu Ser Cys Arg Glu Pro Asn Gln His Phe Lys Pro Tyr
    290                 295                 300

Leu Lys His Phe Leu Pro Lys Arg Leu His Phe Ala Lys Ser Asp Arg
305                 310                 315                 320

Ile Glu Pro Leu Thr Phe Tyr Leu Asp Pro Gln Trp Gln Leu Ala Leu
                325                 330                 335

Asn Pro Ser Glu Arg Lys Tyr Cys Gly Ser Gly Phe His Gly Ser Asp
            340                 345                 350

Asn Val Phe Ser Asn Met Gln Ala Leu Phe Val Gly Tyr Gly Pro Gly
        355                 360                 365

Phe Lys His Gly Ile Glu Ala Asp Thr Phe Glu Asn Ile Glu Val Tyr
    370                 375                 380

Asn Leu Met Cys Asp Leu Leu Asn Leu Thr Pro Ala Pro Asn Asn Gly
385                 390                 395                 400

Thr His Gly Ser Leu Asn His Leu Leu Lys Asn Pro Val Tyr Thr Pro
                405                 410                 415

Lys His Pro Lys Glu Val His Pro Leu Val Gln Cys Pro Phe Thr Arg
            420                 425                 430

Asn Pro Arg Asp Asn Leu Gly Cys Ser Cys Asn Pro Ser Ile Leu Pro
        435                 440                 445

Ile Glu Asp Phe Gln Thr Gln Phe Asn Leu Thr Val Ala Glu Glu Lys
    450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
            500                 505                 510

Arg Asn Asp Ser Phe Ser Thr Glu Asp Phe Ser Asn Cys Leu Tyr Gln
        515                 520                 525

Asp Phe Arg Ile Pro Leu Ser Pro Val His Lys Cys Ser Phe Tyr Lys
    530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
            580                 585                 590

Thr Leu Leu Arg Lys Tyr Ala Glu Glu Arg Asn Gly Val Asn Val Val
        595                 600                 605

Ser Gly Pro Val Phe Asp Phe Asp Tyr Asp Gly Arg Cys Asp Ser Leu
    610                 615                 620

Glu Asn Leu Arg Gln Lys Arg Arg Val Ile Arg Asn Gln Glu Ile Leu
625                 630                 635                 640
```

```
Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Glu Leu Leu Met Leu His Arg Ala Arg Ile Thr
    690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp Glu Pro Lys Ser Cys Asp Lys Thr His Thr Cys Pro Pro
            740                 745                 750

Cys Pro Ala Pro Glu Leu Leu Gly Gly Pro Ser Val Phe Leu Phe Pro
        755                 760                 765

Pro Lys Pro Lys Asp Thr Leu Met Ile Ser Arg Thr Pro Glu Val Thr
    770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
            820                 825                 830

Leu His Gln Asp Trp Leu Asn Gly Lys Glu Tyr Lys Cys Lys Val Ser
        835                 840                 845

Asn Lys Ala Leu Pro Ala Pro Ile Glu Lys Thr Ile Ser Lys Ala Lys
    850                 855                 860

Gly Gln Pro Arg Glu Pro Gln Val Tyr Thr Leu Pro Pro Ser Arg Glu
865                 870                 875                 880

Glu Met Thr Lys Asn Gln Val Ser Leu Thr Cys Leu Val Lys Gly Phe
                885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
        915                 920                 925

Phe Leu Tyr Ser Lys Leu Thr Val Asp Lys Ser Arg Trp Gln Gln Gly
    930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                965                 970


<210> SEQ ID NO 12
<211> LENGTH: 966
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Lys Ser Trp Val Glu Glu Pro Cys Glu Ser Ile Asn Glu Pro Gln
1               5                   10                  15

Cys Pro Ala Gly Phe Glu Thr Pro Pro Thr Leu Leu Phe Ser Leu Asp
```

```
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
    50                  55                  60

Val Tyr Pro Thr Lys Thr Phe Pro Asn His Tyr Ser Ile Val Thr Gly
65                  70                  75                  80

Leu Tyr Pro Glu Ser His Gly Ile Ile Asp Asn Lys Met Tyr Asp Pro
                85                  90                  95

Lys Met Asn Ala Ser Phe Ser Leu Lys Ser Lys Glu Lys Phe Asn Pro
            100                 105                 110

Glu Trp Tyr Lys Gly Glu Pro Ile Trp Val Thr Ala Lys Tyr Gln Gly
        115                 120                 125

Leu Lys Ser Gly Thr Phe Phe Trp Pro Gly Ser Asp Val Glu Ile Asn
    130                 135                 140

Gly Ile Phe Pro Asp Ile Tyr Lys Met Tyr Asn Gly Ser Val Pro Phe
145                 150                 155                 160

Glu Glu Arg Ile Leu Ala Val Leu Gln Trp Leu Gln Leu Pro Lys Asp
                165                 170                 175

Glu Arg Pro His Phe Tyr Thr Leu Tyr Leu Glu Glu Pro Asp Ser Ser
            180                 185                 190

Gly His Ser Tyr Gly Pro Val Ser Ser Glu Val Ile Lys Ala Leu Gln
        195                 200                 205

Arg Val Asp Gly Met Val Gly Met Leu Met Asp Gly Leu Lys Glu Leu
    210                 215                 220

Asn Leu His Arg Cys Leu Asn Leu Ile Leu Ile Ser Asp His Gly Met
225                 230                 235                 240

Glu Gln Gly Ser Cys Lys Lys Tyr Ile Tyr Leu Asn Lys Tyr Leu Gly
                245                 250                 255

Asp Val Lys Asn Ile Lys Val Ile Tyr Gly Pro Ala Ala Arg Leu Arg
            260                 265                 270

Pro Ser Asp Val Pro Asp Lys Tyr Tyr Ser Phe Asn Tyr Glu Gly Ile
        275                 280                 285

Ala Arg Asn Leu Ser Cys Arg Glu Pro Asn Gln His Phe Lys Pro Tyr
    290                 295                 300

Leu Lys His Phe Leu Pro Lys Arg Leu His Phe Ala Lys Ser Asp Arg
305                 310                 315                 320

Ile Glu Pro Leu Thr Phe Tyr Leu Asp Pro Gln Trp Gln Leu Ala Leu
                325                 330                 335

Asn Pro Ser Glu Arg Lys Tyr Cys Gly Ser Gly Phe His Gly Ser Asp
            340                 345                 350

Asn Val Phe Ser Asn Met Gln Ala Leu Phe Val Gly Tyr Gly Pro Gly
        355                 360                 365

Phe Lys His Gly Ile Glu Ala Asp Thr Phe Glu Asn Ile Glu Val Tyr
    370                 375                 380

Asn Leu Met Cys Asp Leu Leu Asn Leu Thr Pro Ala Pro Asn Asn Gly
385                 390                 395                 400

Thr His Gly Ser Leu Asn His Leu Leu Lys Asn Pro Val Tyr Thr Pro
                405                 410                 415

Lys His Pro Lys Glu Val His Pro Leu Val Gln Cys Pro Phe Thr Arg
            420                 425                 430

Asn Pro Arg Asp Asn Leu Gly Cys Ser Cys Asn Pro Ser Ile Leu Pro
        435                 440                 445
```

```
Ile Glu Asp Phe Gln Thr Gln Phe Asn Leu Thr Val Ala Glu Glu Lys
    450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
            500                 505                 510

Arg Asn Asp Ser Phe Ser Thr Glu Asp Phe Ser Asn Cys Leu Tyr Gln
        515                 520                 525

Asp Phe Arg Ile Pro Leu Ser Pro Val His Lys Cys Ser Phe Tyr Lys
    530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
            580                 585                 590

Thr Leu Leu Arg Lys Tyr Ala Glu Glu Arg Asn Gly Val Asn Val Val
        595                 600                 605

Ser Gly Pro Val Phe Asp Phe Asp Tyr Asp Gly Arg Cys Asp Ser Leu
    610                 615                 620

Glu Asn Leu Arg Gln Lys Arg Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Glu Leu Leu Met Leu His Arg Ala Arg Ile Thr
    690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp Asp Lys Thr His Thr Cys Pro Pro Cys Pro Ala Pro Glu
            740                 745                 750

Leu Leu Gly Gly Pro Ser Val Phe Leu Phe Pro Pro Lys Pro Lys Asp
        755                 760                 765

Thr Leu Met Ile Ser Arg Thr Pro Glu Val Thr Cys Val Val Val Asp
    770                 775                 780

Val Ser His Glu Asp Pro Glu Val Lys Phe Asn Trp Tyr Val Asp Gly
785                 790                 795                 800

Val Glu Val His Asn Ala Lys Thr Lys Pro Arg Glu Glu Gln Tyr Asn
                805                 810                 815

Ser Thr Tyr Arg Val Val Ser Val Leu Thr Val Leu His Gln Asp Trp
            820                 825                 830

Leu Asn Gly Lys Glu Tyr Lys Cys Lys Val Ser Asn Lys Ala Leu Pro
        835                 840                 845

Ala Pro Ile Glu Lys Thr Ile Ser Lys Ala Lys Gly Gln Pro Arg Glu
    850                 855                 860
```

```
Pro Gln Val Tyr Thr Leu Pro Pro Ser Arg Glu Glu Met Thr Lys Asn
865                 870                 875                 880

Gln Val Ser Leu Thr Cys Leu Val Lys Gly Phe Tyr Pro Ser Asp Ile
                885                 890                 895

Ala Val Glu Trp Glu Ser Asn Gly Gln Pro Glu Asn Asn Tyr Lys Thr
            900                 905                 910

Thr Pro Pro Val Leu Asp Ser Asp Gly Ser Phe Phe Leu Tyr Ser Lys
        915                 920                 925

Leu Thr Val Asp Lys Ser Arg Trp Gln Gln Gly Asn Val Phe Ser Cys
    930                 935                 940

Ser Val Met His Glu Ala Leu His Asn His Tyr Thr Gln Lys Ser Leu
945                 950                 955                 960

Ser Leu Ser Pro Gly Lys
                965


<210> SEQ ID NO 13
<211> LENGTH: 15
<212> TYPE: PRT
<213> ORGANISM: Homo sapiens

<400> SEQUENCE: 13

Glu Pro Lys Ser Cys Asp Lys Thr His Thr Cys Pro Pro Cys Pro
1               5                   10                  15


<210> SEQ ID NO 14
<211> LENGTH: 10
<212> TYPE: PRT
<213> ORGANISM: Homo sapiens

<400> SEQUENCE: 14

Asp Lys Thr His Thr Cys Pro Pro Cys Pro
1               5                   10


<210> SEQ ID NO 15
<211> LENGTH: 14
<212> TYPE: PRT
<213> ORGANISM: Homo sapiens

<400> SEQUENCE: 15

Pro Lys Ser Cys Asp Lys Thr His Thr Cys Pro Pro Cys Pro
1               5                   10


<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser Gly Gly Gly Gly Ser Gly Gly Gly Gly Ser
1               5                   10                  15


<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

-continued

```
Pro Ser Cys Ala Lys Glu
1               5


<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Asp Asp Asp Asp Asp Asp Asp Asp Asp
1               5                   10


<210> SEQ ID NO 19
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 repeating "Gly
      Gly Gly Gly Ser" units wherein some positions may be absent

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

What is claimed is:

1. A method for [reducing vascular calcification] *treating a subject having Pseudoxanthoma elasticum* (*PXE*), comprising administering to [a] *the* subject [with below normal plasma pyrophosphate (PPi) or above normal serum phosphate (Pi) two or more doses of] *an effective amount of* soluble ectonucleotide pyrophosphatase phosphodiesterase (sNPP1), *fragment or fusion protein thereof*, [wherein each dose contains an amount of sNPP1 that is sufficient to achieve a transient increase in plasma PPi in the subject, the transient increase in plasma PPi characterized by a peak plasma PPi level that is at least about 40% of the normal plasma PPi level and a return to base-line plasma PPi level within about 48 hours after administration of the dose; wherein a) the time period between doses is at least 2 days; b) the normal level of plasma PPi is 2.63±0.47 microMolar; c) the normal level of plasma Pi is 1.5±0.5 milliMolar; and d)] wherein sNPP1 has pyrophosphatase activity, phosphodiesterase activity, or pyrophosphatase and phosphodiesterase activity[, with the proviso that when the sNPP1 is a fusion protein comprising an NPP1 component and one or more fusion partners, each fusion partner is located C-terminally to the NPP1 component].

[2. The method of claim 1, wherein the transient increase in plasma PPi is maintained for at least about 4 hours.]

3. The method of claim 1, wherein the [vascular] *subject has* calcification [is arterial calcification] *of soft tissue*.

4. The method of claim 1, wherein the [vascular calcification is intimal calcification] *subject has calcification of the skin and/or eye(s)*.

[5. The method of claim 1, wherein said subject has NPP1 deficiency.]

[6. The method of claim 1, wherein the subject has chronic kidney disease (CKD) or end-stage renal disease (ESRD).]

[7. The method of claim 1, wherein the subject has generalized arterial calcification of infancy (GACI).]

[8. The method of claim 1, wherein the subject has a cardiovascular disorder, diabetes mellitus II, atherosclerosis, or Pseudoxanthoma elasticum (PXE).]

[9. The method of claim 1, wherein the levels of plasma pyrophosphate (PPi) in the subject before treatment is at least about 40% lower than that of the normal plasma PPi levels.]

10. The method of claim 1, wherein the subject is human.

11. The method of claim 1, wherein [each dose contains] *said effective amount comprises* about [1.0] *0.1* mg/kg to about [10.0] *2.0* mg/kg sNPP1.

[12. The method of claim 1, wherein time period between said sNPP1 doses is at least 3 days.]

13. The method of claim 1, wherein the administration is intravenous, subcutaneous, or intraperitoneal.

14. The method of claim 1, wherein the sNPP1 comprises an isolated recombinant human sNPP1.

15. The method of claim 1, wherein the sNPP1 is a fusion protein comprising a) an NPP1 component that lacks the N-terminal cytosolic and transmembrane domains, and b) a fusion partner located C-terminally to the NPP1 component.

16. The method of claim 15, wherein the fusion protein further comprises a targeting moiety.

17. The method of claim 1, wherein the sNPP1 is SEQ ID NO:3, SEQ ID NO:4, SEQ ID NO:9, SEQ ID NO:10, SEQ ID NO:11 or SEQ ID NO:12.

[18. The method of claim 1, wherein the subject has elevated inorganic phosphate and a ratio of PPi to Pi that is at least 10% higher or lower than normal.]

19. The method of claim 15, wherein the fusion partner comprises the Fc region of an immunoglobulin.

20. The method of claim 15, wherein the fusion protein further comprises a linker, a peptide that targets the fusion protein to sites of calcification, or a linker and a peptide that targets the fusion protein to sites of calcification.

*21. The method of claim 11, where said effective amount comprises 0.5 mg/kg sNPP1.*

*22. The method of claim 11, wherein said effective amount comprises 1.0 mg/kg sNPP1.*

*23. The method of claim 11, wherein said effective amount comprises 5.0 mg/kg sNPP1.*

*24. The method of claim 11, wherein said effective amount comprises 10 mg/kg sNPP1.*

*25. The method of claim 1, wherein said administration is weekly.*

*26. The method of claim 1, wherein said administration is bi-weekly.*

*27. The method of claim 1, wherein said administration is monthly.*

*28. The method of claim 13, wherein said administration is intravenous.*

*29. The method of claim 13, wherein said administration is subcutaneous.*

* * * * *